United States Patent
Nelson et al.

(10) Patent No.: US 10,252,032 B2
(45) Date of Patent: Apr. 9, 2019

(54) SOCKETED PORTAL ANCHORS AND METHODS OF USING SAME

(71) Applicant: Medtronic, Inc., Minneapolis, MN (US)

(72) Inventors: Brian D. Nelson, Birchwood, MN (US); Jeffrey P. Bodner, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 757 days.

(21) Appl. No.: 13/795,487

(22) Filed: Mar. 12, 2013

(65) Prior Publication Data
US 2014/0276416 A1   Sep. 18, 2014

(51) Int. Cl.
| | | |
|---|---|---|
| *A61M 25/00* | (2006.01) | |
| *A61M 25/02* | (2006.01) | |
| *A61M 39/02* | (2006.01) | |
| *A61M 5/142* | (2006.01) | |

(52) U.S. Cl.
CPC ........ *A61M 25/02* (2013.01); *A61M 39/0247* (2013.01); *A61M 5/14276* (2013.01); *A61M 2025/028* (2013.01); *A61M 2025/0286* (2013.01); *A61M 2039/025* (2013.01); *A61M 2039/027* (2013.01); *A61M 2039/0273* (2013.01)

(58) Field of Classification Search
CPC . A61B 19/201; A61B 2019/208; A61B 19/20; A61M 25/02; A61N 1/0539
See application file for complete search history.

(56) References Cited

U.S. PATENT DOCUMENTS

| | | |
|---|---|---|
| 3,021,842 A | 2/1962 | Flood |
| 3,262,452 A | 7/1966 | Hardy et al. |
| 3,444,861 A | 5/1969 | Schulte |
| 3,760,811 A | 9/1973 | Andrew |
| 4,025,964 A | 5/1977 | Owens |
| 4,328,813 A | 5/1982 | Ray |
| 4,350,159 A | 9/1982 | Gouda |
| 4,360,025 A | 11/1982 | Edwards |

(Continued)

FOREIGN PATENT DOCUMENTS

| | | |
|---|---|---|
| DE | 19726141 | 1/1999 |
| DE | 19808220 | 9/1999 |

OTHER PUBLICATIONS

"STIMLOC by ign," datasheet, Image Guided Neurologics, Inc., (c) 2004 Image Guided Neurologics, Inc., Melbourne, FL retrieved from the Internet: <URL: http://www.igneurologics.com/pages/dba2/stimloc.pdf> ; 2 pgs.

*Primary Examiner* — Scott Medway
(74) *Attorney, Agent, or Firm* — Mueting, Raasch & Gebhardt, P.A.

(57) ABSTRACT

Anchors for securing a medical device relative to a body portal, wherein the anchors may accommodate most any implantation trajectory through the portal. Such anchors may further secure the device along any such trajectory without imparting undesirable biasing forces that may shift the device from its intended implanted location. In some embodiments, the anchor is configured as a burr hole anchor including a spherical member contained in a socket of the anchor such that orientation of the spherical member is permitted about three mutually perpendicular axes.

13 Claims, 26 Drawing Sheets

(56) References Cited

U.S. PATENT DOCUMENTS

| | | |
|---|---|---|
| 4,629,451 A | 12/1986 | Winters et al. |
| 4,681,103 A | 7/1987 | Boner et al. |
| 4,805,615 A | 2/1989 | Carol |
| 4,805,634 A | 2/1989 | Ullrich et al. |
| 4,993,425 A | 2/1991 | Kronberg |
| 5,030,223 A | 7/1991 | Anderson et al. |
| 5,263,956 A | 11/1993 | Nobles |
| 5,464,446 A | 11/1995 | Dreessen et al. |
| 5,540,648 A | 7/1996 | Yoon |
| 5,662,600 A | 9/1997 | Watson et al. |
| 5,713,858 A | 2/1998 | Heruth et al. |
| 5,843,150 A | 12/1998 | Dreessen et al. |
| 5,865,842 A | 2/1999 | Knuth et al. |
| 5,916,200 A | 6/1999 | Eppley et al. |
| 5,927,277 A | 7/1999 | Baudino et al. |
| 5,954,687 A | 9/1999 | Baudino et al. |
| 6,044,304 A | 3/2000 | Baudino |
| 6,134,477 A | 10/2000 | Knuteson |
| 6,210,417 B1 | 4/2001 | Baudino et al. |
| 6,321,104 B1 | 11/2001 | Gielen et al. |
| 6,328,748 B1 | 12/2001 | Hennig |
| 6,355,028 B2 * | 3/2002 | Castaneda et al. ............... 606/1 |
| 6,356,792 B1 | 3/2002 | Errico et al. |
| 6,482,182 B1 | 11/2002 | Carroll et al. |
| 6,609,020 B2 | 8/2003 | Gill |
| 6,902,569 B2 | 6/2005 | Parmer et al. |
| 7,004,948 B1 | 2/2006 | Pianca et al. |
| 7,454,251 B2 | 11/2008 | Rezai et al. |
| 7,553,298 B2 | 6/2009 | Hunt et al. |
| 7,580,756 B2 | 8/2009 | Schulte et al. |
| 7,636,596 B2 | 12/2009 | Solar |
| 7,637,915 B2 | 12/2009 | Parmer et al. |
| 7,704,260 B2 | 4/2010 | Skakoon et al. |
| 7,794,469 B2 | 9/2010 | Kao et al. |
| 7,806,886 B2 * | 10/2010 | Kanderian et al. ........... 604/504 |
| 7,828,809 B2 | 11/2010 | Skakoon et al. |
| 7,981,119 B2 | 7/2011 | Lando et al. |
| 7,988,674 B2 | 8/2011 | Adams et al. |
| 8,075,531 B2 | 12/2011 | Davey |
| 8,603,038 B2 | 12/2013 | Nelson |
| 8,738,151 B2 | 5/2014 | Nelson |
| 2002/0019641 A1 | 2/2002 | Truwit |
| 2002/0042605 A1 * | 4/2002 | Castaneda et al. ............... 606/1 |
| 2002/0052610 A1 | 5/2002 | Skakoon et al. |
| 2002/0151871 A1 | 10/2002 | Gaiser et al. |
| 2002/0169460 A1 | 11/2002 | Foster et al. |
| 2003/0040753 A1 | 2/2003 | Daum et al. |
| 2003/0114752 A1 | 6/2003 | Henderson et al. |
| 2003/0199831 A1 | 10/2003 | Morris et al. |
| 2004/0034367 A1 | 2/2004 | Malinowski |
| 2004/0243146 A1 | 12/2004 | Chesbrough et al. |
| 2004/0267284 A1 * | 12/2004 | Parmer et al. ............... 606/130 |
| 2005/0054985 A1 | 3/2005 | Mogg |
| 2005/0125007 A1 | 6/2005 | Gill |
| 2005/0143799 A1 | 6/2005 | Black et al. |
| 2005/0143800 A1 | 6/2005 | Lando et al. |
| 2005/0182464 A1 | 8/2005 | Schulte et al. |
| 2005/0192594 A1 | 9/2005 | Skakoon et al. |
| 2006/0111688 A1 | 5/2006 | Kraus et al. |
| 2006/0129126 A1 | 6/2006 | Kaplitt et al. |
| 2007/0149977 A1 | 6/2007 | Heavener |
| 2008/0200798 A1 | 8/2008 | Ecklund et al. |
| 2009/0187149 A1 | 7/2009 | Nelson |
| 2009/0306501 A1 | 12/2009 | Flint |
| 2010/0042111 A1 | 2/2010 | Qureshi et al. |
| 2010/0174240 A1 | 7/2010 | Wells et al. |
| 2010/0217196 A1 | 8/2010 | Nelson |
| 2010/0312280 A1 | 12/2010 | Overes et al. |
| 2011/0270187 A1 | 11/2011 | Nelson |
| 2012/0083742 A1 | 4/2012 | Nelson |
| 2013/0072876 A1 | 3/2013 | Pretre et al. |
| 2014/0276418 A1 | 9/2014 | Nelson et al. |
| 2014/0276529 A1 | 9/2014 | Bodner |

* cited by examiner

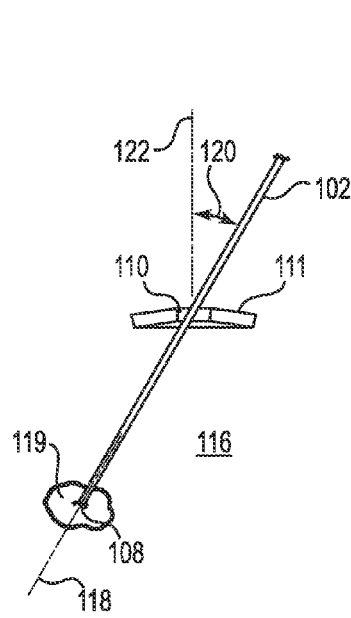
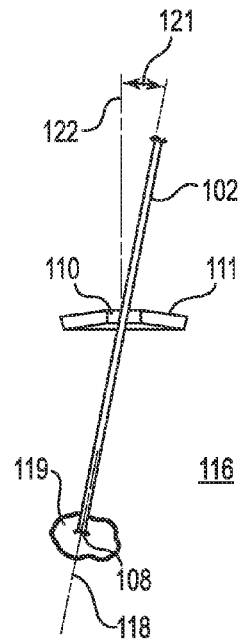
Fig. 2　　　Fig. 3
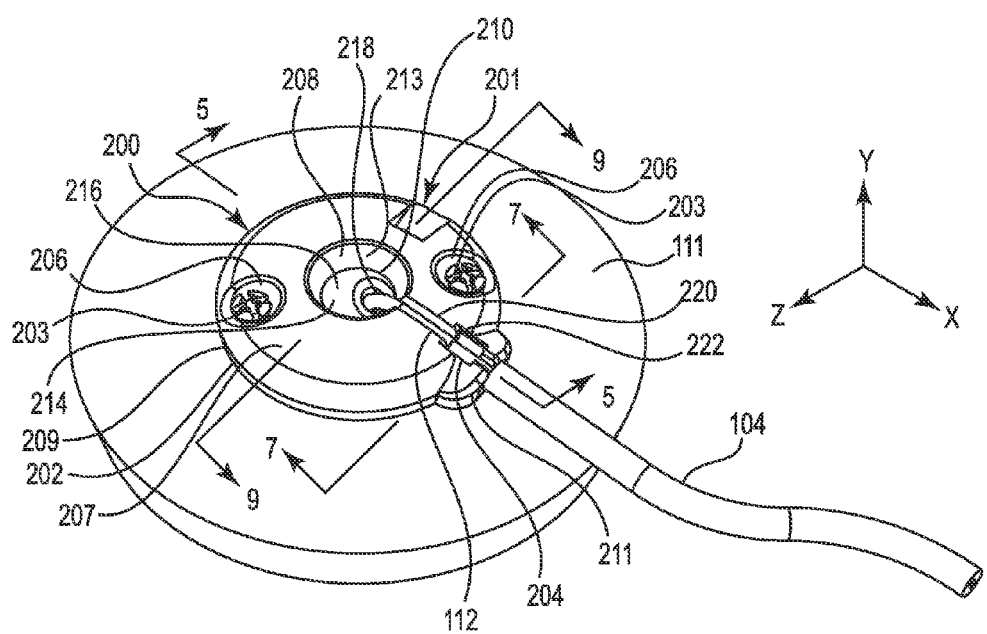
Fig. 4

SOCKETED PORTAL ANCHORS AND METHODS OF USING SAME

Embodiments of the present invention relate generally to medical devices and, more particularly, to anchors for securing a therapy delivery device (e.g., a catheter or lead) within, or otherwise relative to, a body portal such as a cranial burr hole, and to systems and methods incorporating such anchors.

BACKGROUND

Medical procedures involving insertion of a medical device into the brain (through a burr hole formed in the skull) are used to treat a variety of medical conditions. For example, electrical stimulation of the brain to relieve chronic pain, or for the treatment of movement disorders, may necessitate the implantation, via the burr hole, of an electrode or lead. Similarly, burr holes are typically formed to allow implantation of a therapy catheter, e.g., an intraparenchymal (IPA) or intracerebroventricular catheter, to treat various ailments.

Use of such devices to deliver therapy to the brain generally involves the insertion of the device into the brain through the burr hole and positioning a distal, therapy delivery tip of the device at a desired target tissue location. During a typical implantation procedure, an incision is made in the scalp to expose the patient's skull. After forming a burr hole through the skull, the device is inserted into the brain. To accurately place the device, surgeons typically use stereotactic apparatus/procedures. One exemplary stereotactic apparatus is described in U.S. Pat. No. 4,350,159 to Gouda, which may be used to position, for example, an electrode.

As one can appreciate, once an inserted device such as a catheter is properly positioned, it is important that it be adequately immobilized to prevent movement of its distal tip from its intended location. Such movement may result in undesirable lateral forces applied by the implanted medical device to brain tissue, especially near the entry point (cortex). Moreover, even minimal movement of the device's distal tip may reduce therapeutic efficacy. Accordingly, reliable methods and apparatus for anchoring and securing the device relative to the burr hole are desirable.

After locating the distal tip at the target tissue location, a portion of the medical device that extends outside of the burr hole may be anchored using an anchor device. A proximal end of the medical device may then connect to a therapeutic source (e.g., for a catheter, to a reservoir containing a therapeutic agent; for a lead, to an electrical stimulation source). For example, when the medical device is a therapy catheter, the proximal end of the therapy catheter may connect to a second, delivery or pump catheter that is, in turn, coupled to an implantable pump containing the therapeutic agent. As a result, the agent may be delivered through the delivery catheter and the therapy catheter to the desired target tissue location within the patient.

Increasingly, surgeons desire access to the brain via device trajectories that are angled relative to the burr hole. That is, some surgeries may benefit from insertion of the medical device into the brain at an angle that is canted from (e.g., not aligned with) an axis normal to the skull surface at the burr hole. Many existing burr hole anchors, however, are configured to grip or secure the medical device assuming that its orientation is normal to the skull surface. In the case of an angled implant trajectory, such anchors may impart clamping forces that potentially bias the device away from its original implant trajectory, and thus bias the therapy delivery tip away from the intended target tissue location. This result may be amplified with increased trajectory angle, stiffer medical devices, and shallower insertion depths.

SUMMARY

The present invention may overcome these and other issues by providing, in one embodiment, a sub-dermal anchor configured to secure a medical device implanted via a portal formed in a mammalian body. The anchor may include a base configured to secure to tissue surrounding the portal, wherein the base has an upper side, lower side, outer edge, and inner edge. The inner edge may define an opening passing between the upper and lower sides, wherein the opening forms a socket. An elastomeric retention member may also be provided, wherein the retention member includes a spherical surface. The retention member may be configured to be received within the socket such that the retention member may rotate therein about three mutually perpendicular axes. The retention member defines a bore formed therethrough, the bore configured to permit passage of the medical device through the base from the upper side to the lower side. The retention member is positioned within the socket such that an uppermost surface of the retention member is at an elevation below the upper side of the base.

In another embodiment, a burr hole anchor is provided and configured to secure a medical device implanted through a burr hole. The anchor may include a base configured to secure to bone surrounding the burr hole, the base having an upper side, lower side, outer edge, and inner edge, the inner edge defining an opening passing between the upper and lower sides, wherein the opening forms a socket. Also included is an elastomeric spherical member configured to be received within the socket such that the spherical member may rotate therein. The spherical member may define a bore formed therethrough, the bore configured to permit passage of the medical device through the base from the upper side to the lower side. The spherical member is configured to immobilize the medical device via application of a radial compression force applied to the medical device.

In another embodiment, a method for anchoring a medical device relative to a body portal of a patient is provided. The method may include: aligning a guide cannula with the body portal such that a trajectory of the guide cannula intersects a target tissue location within the patient; and inserting a distal tip of the guide cannula through a bore formed in a portal anchor and sliding the portal anchor along the guide cannula. The anchor may include a base configured to secure to tissue surrounding the portal, wherein the base includes an upper side, lower side, outer edge, and inner edge. The inner edge may define an opening passing between the upper and lower sides, the opening forming a socket. An elastomeric spherical member may also be provided and configured to be received within the socket such that the spherical member may rotate therein about three mutually perpendicular axes, wherein the spherical member may define the bore for receiving the guide cannula. The method further includes: positioning the guide cannula so that the distal tip is inside the body portal; sliding the anchor towards the distal tip of the guide cannula until the base of the anchor reaches the tissue surrounding the body portal; rotating the spherical member relative to the base until the base is flush with the tissue surrounding the body portal; and attaching the base to the tissue.

In yet another embodiment, an infusion system is provided including a therapy catheter implantable through a burr hole, wherein the therapy catheter includes a therapy delivery end configured to be positioned at a target tissue location. A delivery catheter is also provided and operable to deliver a therapeutic agent, from a source containing the therapeutic agent, to the therapy catheter. A connector configured to fluidly couple the therapy catheter with the delivery catheter may also be included. The system may also include an anchor including a base configured to secure to bone surrounding the burr hole, wherein the base has an upper side, lower side, outer edge, and inner edge, the inner edge defining an opening passing between the upper and lower sides, wherein the opening forms a socket. The anchor may further include a spherical member configured to be received within the socket such that the spherical member may rotate therein about three mutually perpendicular axes. The spherical member may define a bore therein, the bore configured to receive both a first end of the therapy catheter and a first end of the connector when the first end of the connector is fluidly coupled to the therapy catheter.

In still yet another embodiment, an infusion system is provided that includes a therapy catheter implantable through a burr hole, wherein the therapy catheter includes a therapy delivery end configured to be positioned at a target tissue location. A delivery catheter may also be included and operable to deliver a therapeutic agent, from a source containing the therapeutic agent, to the therapy catheter. A connector may be provided to fluidly couple the therapy catheter with the delivery catheter. The system may also include an anchor having a base configured to secure to bone surrounding the burr hole. The base may include an upper side, lower side, outer edge, and inner edge, the inner edge defining an opening passing between the upper and lower sides, wherein the opening forms a socket. The anchor may further include an elastomeric spherical member configured to be received within the socket such that the spherical member may rotate therein. The spherical member may define a bore formed therethrough, the bore configured to permit passage of the therapy catheter through the base from the upper side to the lower side, wherein the spherical member is configured to immobilize the therapy catheter via application of a radial compression force applied to the therapy catheter.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIGS. 2-3 illustrate diagrammatic views of a trajectory of an implanted medical device in two orthogonal planes, wherein:

FIG. 2 illustrates the device trajectory when viewed normal to a first (e.g., sagittal) plane; and FIG. 3 when viewed normal to a second, intersecting and orthogonal (e.g., coronal) plane;

FIG. 4 is a perspective view of an portal anchor (e.g., burr hole anchor) in accordance with one embodiment of the invention;

FIGS. 18-23 illustrate diagrammatically an exemplary method for using the anchors illustrated in the previous figures, wherein:

FIG. 18 illustrates initial attachment of the anchor to a guide cannula;

FIG. 19 illustrates movement of the anchor to a tissue (e.g., skull) surface;

FIG. 20 illustrates attachment of the anchor to the tissue;

FIG. 21 illustrates immobilization of a retention member of the anchor;

FIG. 22 illustrates insertion of the medical device; and

FIG. 23 illustrates removal of the guide cannula;

FIGS. 29-34 illustrate an exemplary diagrammatic method for using the anchor illustrated in FIG. 24-28 to anchor a therapy catheter, wherein:

FIG. 29 is a partial perspective view illustrating an exemplary method of securing a guide cannula relative to a spherical member of the anchor;

FIG. 30 shows removal of the guide cannula after insertion of the therapy catheter;

FIG. 31 is a partial perspective view illustrating how the therapy catheter may be secured relative to the spherical member once the guide cannula is retracted;

FIG. 32 is a section view illustrating coupling of a connector to the therapy catheter;

FIG. 33 is a perspective view illustrating the anchor after the connector and therapy catheter are coupled; and FIG. 34 is a perspective view illustrating coupling of the connector with a delivery catheter;

FIGS. 43-49 illustrate diagrammatically an exemplary method for using the anchor shown in FIGS. 38-42, wherein:

FIG. 43 illustrates initial attachment of the anchor to a guide cannula;

FIG. 44 illustrates movement of the anchor to a tissue (e.g., skull) surface;

FIG. 45 illustrates initial attachment of the anchor to the tissue;

FIG. 46 illustrates removal of the guide cannula after insertion of a medical device;

FIG. 47 illustrates immobilization of a retention member of the anchor;

FIG. 48 illustrates final attachment of the anchor to the tissue and attachment of an optional cap; and FIG. 49 illustrates a bottom perspective view of the optional cap;

Figure 1:
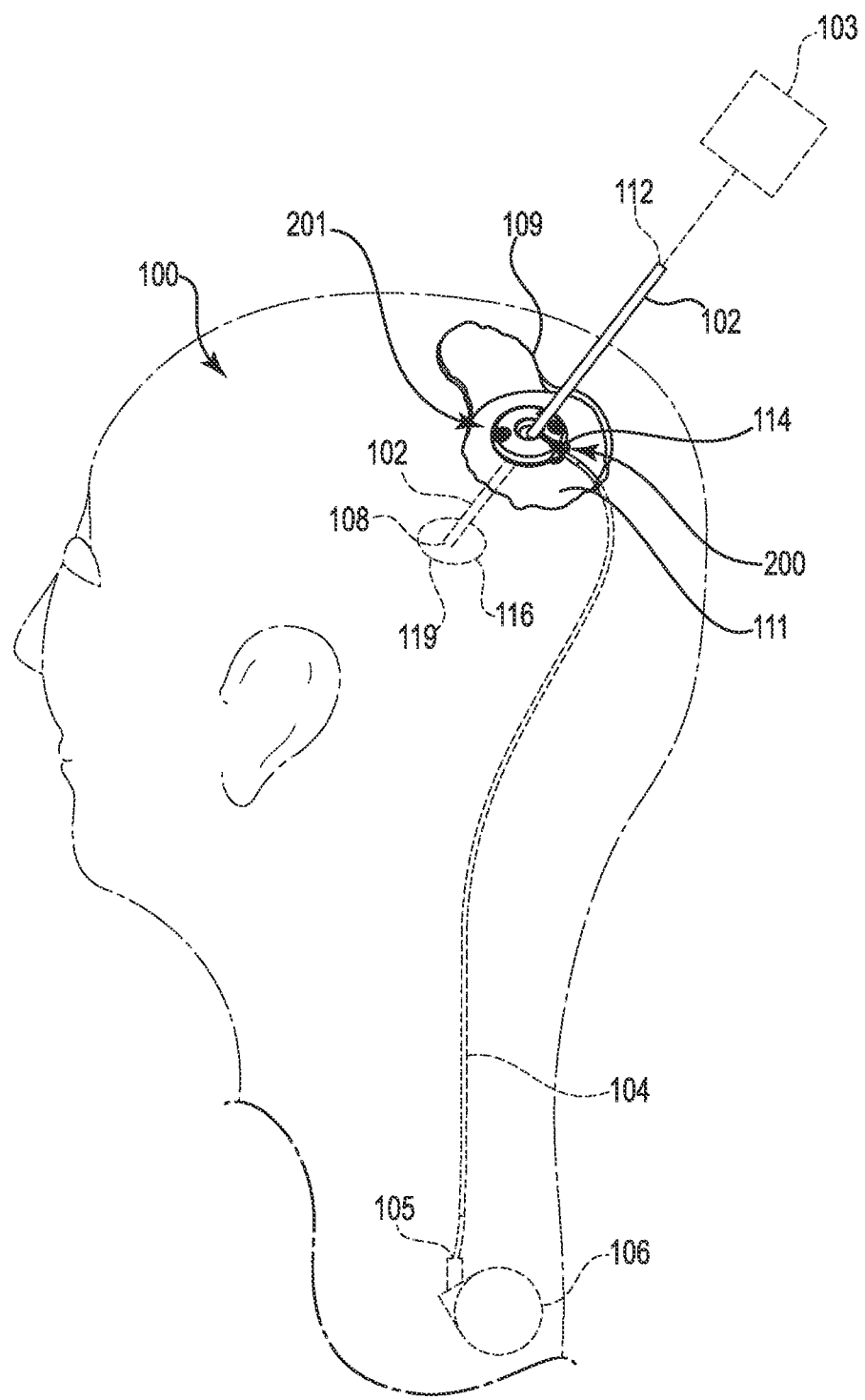
FIG. 1 illustrates an exemplary implantable infusion system, the system including an anchor system in accordance with one embodiment of the invention.

The figures are rendered primarily for clarity and, as a result, are not necessarily drawn to scale. Moreover, various structure/components, including but not limited to fasteners, electrical components (wiring, cables, etc.), and the like, may be shown diagrammatically or removed from some or all of the views to better illustrate aspects of the depicted embodiments, or where inclusion of such structure/components is not necessary to an understanding of the various exemplary embodiments of the invention. The lack of illustration/description of such structure/components in a particular figure is, however, not to be interpreted as limiting the scope of the invention in any way.

DETAILED DESCRIPTION OF EXEMPLARY EMBODIMENTS

In the following detailed description of illustrative embodiments of the invention, reference is made to the accompanying figures of the drawing which form a part hereof and in which are shown, by way of illustration, specific embodiments in which the invention may be practiced. It is to be understood that other embodiments may be utilized and structural changes may be made without departing from the scope of the present invention.

Embodiments of the instant invention may be directed to body portal anchor devices and assemblies and to corresponding body portal anchor systems and methods for securing a medical device such as a therapy catheter or stimulation lead relative to a body portal. For example, exemplary anchors described herein may be configured to secure a therapy device such as an IPA therapy catheter routed through a cranial burr hole. Such embodiments may further provide for connection of the therapy catheter with a delivery catheter that is fluidly connected to a therapy source. While embodiments described herein may find use in acute treatment, they are particularly advantageous for long-term implantation, e.g., lasting several weeks or longer. Accordingly, devices in accordance with embodiments of the instant invention provide a low profile, allowing them to be located sub-dermally, potentially for an indefinite period of time, e.g., seven years or more.

Systems in accordance with embodiments of the present invention may permit substantial isolation of the medical device (e.g., therapy catheter or lead) from forces that may act outside of the body portal, e.g., forces acting upon the delivery catheter connected to the therapy catheter. Moreover, systems, anchors, and methods in accordance with embodiments of the present invention may accommodate implantation trajectories along most any axis through the burr hole. That is, anchors like those described herein may receive and secure the medical device along most any trajectory (e.g., normal to the skull or otherwise) and may further secure the device along such a trajectory without imparting excessive biasing forces that may shift the device from its implanted location or apply lateral pressure against tissue (e.g., against the cortex).

While exemplified herein in the context of burr hole anchors and corresponding infusion/electrical stimulation systems, anchors and systems in accordance with embodiments of the present invention may be advantageous for other applications. In fact, while described herein with reference to the treatment of neurological disorders, embodiments of the present invention may find use in most any system (e.g., medical or otherwise) that would benefit from portal anchoring of an elongate member.

It is noted that the terms "comprises" and variations thereof do not have a limiting meaning where these terms appear in the accompanying description and claims. Further, "a," "an," "the," "at least one," and "one or more" are used interchangeably herein. Moreover, relative terms such as "left," "right," "front," forward," "aft," "rear," "rearward," "top," "bottom," "side," "upper," "lower," "above," "below," "horizontal," "vertical," and the like may be used herein and, if so, are from the perspective observed in the particular figure (or as observed when the apparatus is in a typical use orientation). These terms are used only to simplify the description, however, and not to limit the scope of the invention in any way.

With reference to the drawing, wherein like reference numerals designate like parts and assemblies throughout the several views, FIG. 1 diagrammatically illustrates an exemplary implantable medical system such as a brain infusion system 100 as it may be configured during use, e.g., implantation. Exemplary embodiments of the components described and illustrated herein may be sized for use with burr holes typical in human and other mammalian (e.g., primate) applications. For example, in one embodiment, a diameter of the burr hole 110 (see, e.g., FIG. 2) may be anywhere from about 6 millimeters (mm) to about 14 mm in diameter. However, such a configuration is not limiting as exemplary anchors could be scaled to accommodate most any size portal without departing from the scope of the invention.

The exemplary infusion system 100 may include a therapy source 106, and an anchor system 201. The anchor system may include a cranial burr hole anchor device or assembly (referred to herein as "anchor 200") and, in some embodiments, a first medical tube, e.g., an intra-cranial IPA therapy catheter 102. The therapy catheter 102 may be partially implanted within a mammalian (e.g., human) brain 116 such that a distal, therapy delivery tip or end 108 is located at a target tissue location 119 in the brain.

To assist with placement of the therapy catheter 102, a stereotactic apparatus (diagrammatically illustrated by reference number 103) as is known in the art may be utilized (see, for example, U.S. Pat. Pub. No. 2012/0083742 to Nelson). In the illustrated example, the therapy catheter 102 is implanted through a body portal, e.g., through a burr hole 110 (the burr hole is located underneath a burr hole anchor 200 in FIG. 1; but see FIGS. 2 and 5). The burr hole 110 may be formed in tissue (e.g., the bone forming the skull 111, which is shown underneath the scalp 109, the scalp being shown peeled back to provide access to the skull in FIG. 1).

Once the catheter 102 is accurately implanted through the burr hole in the skull (i.e., once the therapy delivery tip 108 is positioned at the predetermined target tissue location 119 in the brain 116), a proximal portion of the catheter 102 (the portion extending outside the burr hole) may be anchored with an anchor (anchor 200) in accordance with embodiments of the present invention.

A first end 112 of the therapy catheter 102 may be routable through the anchor 200. In the illustrated embodiment, the first end 112 of the therapy catheter 102 (after disconnecting from the stereotactic apparatus and trimming to an appropriate length) may be operatively connected to a corresponding first end 114 of a feed or delivery catheter 104 (e.g., via a connector associated with the anchor, exemplary embodiments of which are described below) of the system 100/anchor system 201.

The delivery catheter 104 may have a second end 105 coupled to a therapy source or reservoir (e.g., an implantable infusion pump 106 such as a SynchroMed® II programmable infusion pump distributed by Medtronic, Inc., of Minneapolis, Minn. USA) containing a volume of the therapeutic agent. While described and illustrated herein utilizing an implantable infusion pump, this configuration is not limiting. For example, other embodiments may replace the pump with most any internal or external medicament delivery device, e.g., syringe, drip bag, etc.

The infusion system 100 may, in one embodiment, be configured to deliver a therapeutic agent for the treatment of a chronic ailment, e.g., convection-enhanced delivery (CED) of a therapeutic agent for the treatment of Huntington's disease. The therapeutic agent is delivered, via the catheters 102 and 104, from the pump 106 to the target tissue location 119 of the brain 116. This application is not limiting, however, as the system may be configured to deliver other therapeutic agents (e.g., such as for the treatment of Parkinson's or Alzheimer's disease) to the brain or to most any other region of the body.

As used herein, "therapeutic agents" may be a generic term referring to a fluid containing pharmaceutical compositions, genetic materials, biologics, and other substances. Pharmaceutical compositions may include, for example, antispasmodics, pain medications, chemotherapeutic agents, and the like. Genetic materials include substances intended to have a direct or indirect genetic therapeutic effect such as genetic vectors, genetic regulator elements, genetic structural elements, DNA, and the like. Biologics include substances that are living matter or derived from living matter intended to have a therapeutic effect such as stem cells, platelets, hormones, biologically produced chemicals, and the like. Other substances may include those that do not have a direct therapeutic effect such as, saline solutions, fluoroscopy agents, disease diagnostic agents, and the like. Accordingly, unless otherwise noted, the terms "therapeutic agent," "therapeutic substance," "drug," or "fluid" may be used interchangeably herein and may include most any therapeutic, diagnostic, or other substance that is delivered using the implantable systems and methods described herein.

Once again, while described above in the context of catheter implantation, the system 100, including the anchor 200, could also be configured to anchor an electrical element such as a stimulation lead. That is, the system could be an electrical stimulation lead system 100 in which a lead 102 is implanted such that its distal end 108 is positioned at the desired target tissue location 119. A proximal end 112 of the lead 102 could then, after disconnection from the stereotactic apparatus 103, be tunneled beneath the scalp 109 and connected to an electrical stimulation source 106 (in this embodiment, the lead 102 may connect to an intermediate extension 104 that, in turn, connects to the electrical stimulation source 106).

With this general overview, the following description addresses various embodiments and aspects of exemplary anchors systems, as well as methods for using the same. While these embodiments may be described with some degree of particularity, they are nonetheless exemplary. That is, those of skill in the art will recognize that other embodiments are certainly possible without departing from the scope of the invention. Moreover, unless clearly stated otherwise, the actual medical device described and/or illustrated in conjunction with any specific embodiment herein may be either a therapy catheter or an electrical lead. As a result, the terms "medical device" (or "device"), "therapy catheter" (or "catheter"), and "electrical lead" (or "lead") may be used herein to refer to most any elongate member.

FIGS. 2 and 3 are exemplary diagrammatic illustrations of the medical device 102 implanted through the burr hole 110 formed in the skull 111 (anchor 200 removed for clarity in these views), with FIG. 2 showing a view looking normal to a first (e.g., sagittal) plane and FIG. 3 showing a view looking normal to a second intersecting, orthogonal (e.g., coronal) plane. As clearly indicated in these views, the stereotactically-guided trajectory 118 (which may also be referred to herein as an "axis" 118) of the device 102 may be selected to intersect the target tissue location 119 within the brain 116. As further illustrated in these views, the trajectory 118 may be along an axis that is slanted relative to a line 122 normal to the tissue (e.g., slanted relative to a line normal to the skull bone) surrounding the burr hole. That is, the trajectory 118 may be oriented such that it is neither coaxial nor parallel to an axis (the axis being coincident and co-identified with line 122) of the burr hole 110.

For instance, when viewed normal to the first (e.g., sagittal) plane as shown in FIG. 2, the trajectory axis 118 is slanted at an angle 120 from the axis 122. Moreover, the trajectory 118 may also be slanted, relative to the axis 122, when viewed normal to the second (e.g., coronal) plane at an angle 121. That is to say, the trajectory 118 may be skewed from normal relative to one or both of these mutually perpendicular planes. Anchors in accordance with embodiments of the present invention are configured to secure the medical device, without undesirably imparting anchor forces that could ultimately bias the therapy delivery tip 108 away from the target tissue location 119. This advantage may be realized regardless of whether the device trajectory 118 is parallel to the axis 122, or is instead slanted (in one or both planes) relative to the axis such as illustrated in FIGS. 2 and 3. While not wishing to be bound to any particular orientation, the angles 120 and 121 could be about 30 degrees or less, e.g., 25 degrees or less.

FIGS. 4-9 illustrate various views of the anchor system 201 including the burr hole anchor 200 in accordance with one exemplary embodiment of the invention. With reference to FIG. 4, the anchor 200 may include an annular base 202 that may be positioned to surround the burr hole 110 (covered by the anchor in FIG. 4, but see FIG. 5). The anchor 200 (e.g., the base 202) is operable to secure to the tissue, e.g., to an outer surface of the bone (skull 11), surrounding the burr hole 110 via any acceptable method. In the illustrated embodiment, the base 202 is secured with bone screws 203 extending through openings (e.g., holes 206) formed through the base 202 and threaded into the skull 111.

Figure 5:
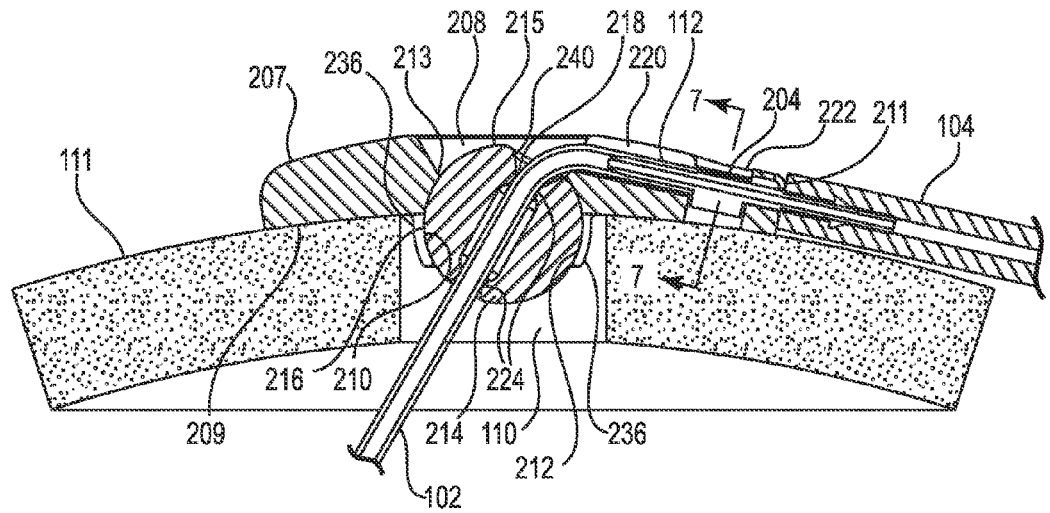
FIG. 5 is a section view taken along line 5-5 of FIG. 4.
Figure 8:
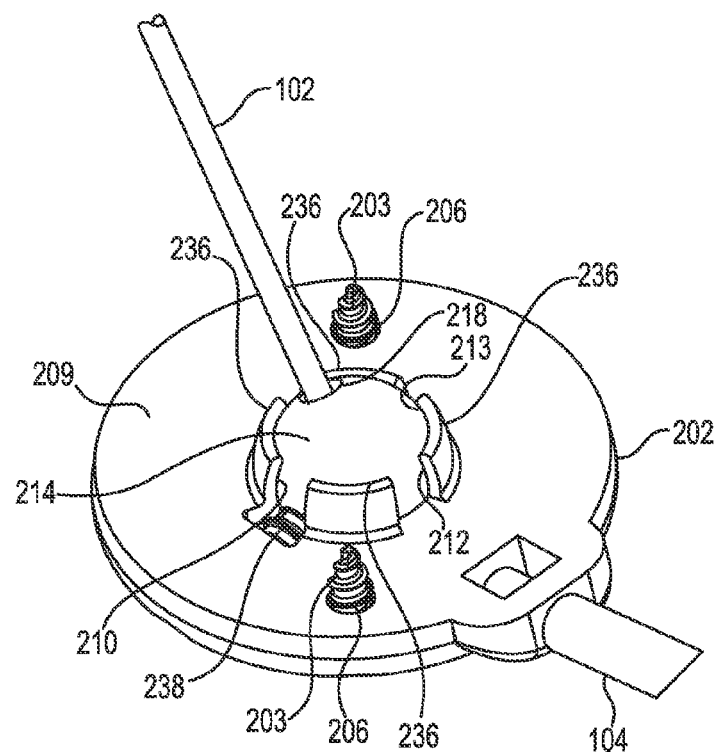
FIG. 8 is a bottom perspective view of the anchor of FIG. 4.
Figure 9:
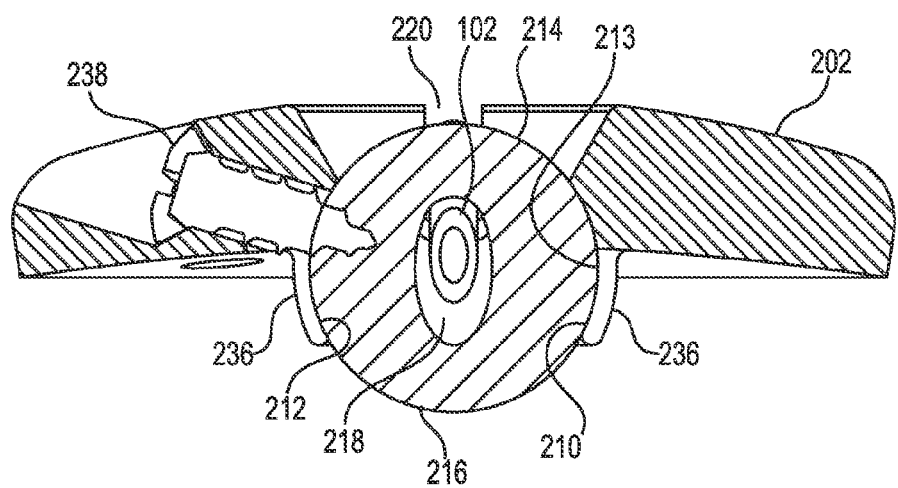
FIG. 9 is a section view taken along line 9-9 of FIG. 4.

The base 202 may include an upper side 207, a lower side 209, a peripheral or outer edge 211, and an inner edge 213. The inner edge 213 may define an opening 208 passing through the base 202 between the upper and lower sides 207 and 209, wherein the inner edge further defines a socket 210 as is also shown in FIGS. 5 and 8-9. The socket 210 may be configured to receive therein a retention member that forms or otherwise includes a convex or spherical surface 216 (see also FIG. 5). In the embodiment illustrated in FIGS. 4-9, the retention member may be configured as a ball-shaped or spherical member 214, while in other embodiments the retention member may merely incorporate one or more portions that define a spherical surface. As used herein, the term "spherical member" includes any retention member forming or incorporating a spherical surface, whether or not the retention member is actually ball-shaped.

The retention member (e.g., spherical member 214) is configured to be received within the socket 210 such that the retention member is operable, under certain circumstances, to rotate therein about three mutually perpendicular axes represented in FIG. 4 by axes x, y, and z.

The spherical member 214 may define a bore 218 formed therethrough. The bore 218 is configured to permit passage of the medical device (e.g., catheter or lead 102 as shown in FIG. 5) through the base 202 from the upper side 207 to the lower side 209. Moreover, in the illustrated embodiment, the spherical member 214 is positioned within the socket 210 such that an uppermost surface 215 of the retention member is at an elevation below the upper side 207 of the base as best seen in FIG. 5. As with the other embodiments described herein, the anchor 200 may provide a low profile as also shown in FIG. 5. This is partially accomplished by recessing the spherical member 214 into the burr hole as shown. While not wishing to be bound to any particular height, the anchor may, in one embodiment, extend above the surface of the skull 111 a distance of about 2-3 mm, e.g., about 2.5 mm.

As shown in FIG. 5, the opening 208 formed in the base 202 may be positioned to align coaxially with the burr hole 110. The upper side 207 of the base 202 may also define a passage, e.g., groove 220, extending from the inner edge 213 to and through the outer edge 211. The groove 220 may define a channel configured to receive therein the medical device 102 during device anchoring. For example, when used with a therapy catheter 102, the groove 220 may receive therein the proximal end 112 of the therapy catheter 102. The groove 220 may be configured in most any acceptable manner that provides a passage or channel extending from the opening 208 through the peripheral or outer edge 211. In the illustrated embodiment, the groove 220 is configured as a relatively open-faced trough as shown in FIGS. 4 and 5. The groove 220 may be further defined by an enlarged section or relief 222, the purpose of which is explained in more detail below.

While shown herein as a trough-like groove 220 (see, e.g., FIG. 5), the passage could alternatively pass completely through the base (form a slot extending between the upper and lower sides) as shown, for example, with slot 820 in FIG. 5l.

Figure 6:
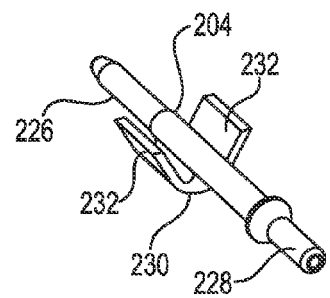
FIG. 6 is a perspective view of a connector of the anchor of FIG. 4.
Figure 7:
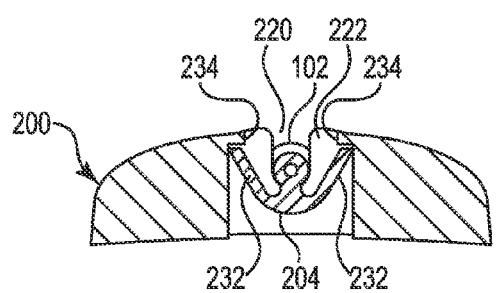
FIG. 7 is a section view taken along line 7-7 of FIG. 4.

In addition to selectively receiving the catheter 102, the trough-like groove 220 may also selectively receive therein a tubular pin or connector 204, which is illustrated separately in FIG. 6. The connector 204 is configured for use with the anchor 200 when the latter is used to secure a therapy catheter (i.e., the connector may not be required when the medical device 102 is configured as an electrical lead).

As shown in FIG. 6, the connector 204 may include a first end 226 defining a therapy tip, and an opposite or second end 228 defining a delivery tip. The connector 204 may further include an enlarged central portion 230 between the first and second ends. The first and second ends 226, 228 (e.g., the therapy tip and the delivery tip) may be configured for insertion into lumens of, respectively, the therapy catheter 102 and the delivery catheter 104. The shape and size of the first and second ends of the connector 204, as well as the size and material of the catheters, may be selected to produce a relatively secure and leak-free connection between the catheters and the connector when joined. The connector 204 is hollow to permit passage of fluid from the delivery catheter 104 to the therapy catheter 102.

The central portion 230 of the connector 204 may further include one or more retaining elements, which in one embodiment, are configured as diverging protrusions 232. The protrusions 232 may be designed to engage the relief 222 of the groove 220 as shown in the section view of FIG. 7 (some anchor structure removed from this view for clarity). That is (as further described below), once the therapy catheter 102 is connected to the first end 226 of the connector 204, the connector may be placed into the groove 220 and pushed (downwardly in FIG. 7) until the protrusions 232 deflect and engage overhanging portions 234 of the base within the relief 222, e.g., with a snap-fit. Once the connector 204 is received in this manner, it is captivated or immobilized, relative to the base 202, from axial, transverse, and rotational movement. Such immobilization may prevent, or at least reduce, forces from being transmitted between the delivery catheter 104 and the therapy catheter 102 that could dislodge the therapy delivery tip 108.

As used herein, the term "immobilize" and its variations refers to securing a first member to one or more second members such that little or no relative movement occurs between the first and second members. Those of skill in the art will realize that, for a variety of reasons (e.g., tolerances of parts), some minor relative movement may still occur between the members, but such movement is minimized and of little or no consequence to the intended operation of the immobilized member.

While most any biocompatible material is suitable, the base 202 may, in one embodiment, be made from a moldable thermoplastic (e.g., polysulfone or polyetheretherketone (PEEK)) or metal such as grade 2 or grade 5 Titanium. The connector 204 may be made of the same or similar material. The retention member (e.g., spherical member 214) however, for reasons that will become apparent, may be made of a softer elastomeric material such as silicone or urethane (e.g., 55D urethane).

FIGS. 5 and 8-9 illustrate additional details regarding the exemplary retention member (e.g., spherical member 214) and its interaction with the socket 210 of the base 202. As evident in these views, the inner edge 213 that forms the socket 210 may itself form a concave or spherically-shaped surface 212 such that the spherical member 214 is received and retained therein. To accommodate the spherical member 214, the inner edge 213 may include two or more (e.g., four) downwardly protruding segments 236 (see FIG. 8) that at least partially form the socket 210. The segments 236 may be sufficiently deflectable to permit assembly (i.e., insertion of the spherical member 214 into the base 202) of the anchor 200 during manufacture/assembly.

In the illustrated embodiments, the socket 210 is designed to accommodate the spherical member 214 with clearance or slight interference such that the spherical member may rotate within the socket during the surgical implant process. That is, the socket 210 may be sized such that the spherical member 214 may rotate therein about the three mutually perpendicular axes (see, e.g., axes x, y, and z of FIG. 4). As a result, the spherical member 214 (and thus the bore 218) may be oriented as needed, relative to the base 202, during implantation and the spherical member may stay aligned with the trajectory 118 during fixation of the base 202 to the skull 111. However, the anchor 200 may also include a lock member to lock the spherical member 214 relative to the base 202 once the desired trajectory of the catheter is set. In the illustrated embodiment, the lock member may be configured as a fastener (e.g., a bone screw 238) that passes through the base 202 (e.g., with clearance) and protrudes therefrom into the socket 210 as best shown in FIGS. 8 and 9. When the screw 238 is tightened, it penetrates, e.g., threads into or "taps," the spherical member 214 as shown in FIG. 9. Stated alternatively, once the catheter 102 is implanted aid and the base 202 is secured to the skull 111 (e.g., via the bone screws 203 (see FIG. 4), the spherical member 214 may be immobilized relative to the base 202 by tightening the screw 238. A length of the screw 238 may be selected such that its distal tip (the tip contacting/penetrating the spherical member) cannot extend into the bore 218 of the spherical member 214 even when the screw 238 is fully tightened.

The retention member may have various constructions. For instance, in the embodiment of FIGS. 4-9, the bore 218 may be formed (e.g., molded) as either a constant diameter extending through the spherical member 214, or alternatively, as a stepped diameter as seen most clearly in FIG. 5. The stepped diameter may be used to control the area of engagement between the spherical member 214 and the medical device (e.g., catheter 102). For example, in the illustrated embodiment, the stepped diameter provides two discrete circumferential areas 224 of contact (e.g., the areas 224 define continuous rings of contact) between the spherical member 214 and the catheter, although any number of discrete contact areas is possible. These contact areas 224 apply a compression radial force to the catheter 102 (and, as described below, to a guide cannula used when inserting the catheter) to secure the catheter relative to the spherical member 214. In other embodiments, the areas 224 may be segmented or broken such that the area in contact with the medical device is discontinuous.

The bore 218 may further include a chamfer or radius 240 near the uppermost surface 215 as shown in FIG. 5 to reduce the occurrence of pinching or kinking of the medical device and to assist with placing the catheter 102 into bore 218 and then into the groove 220. As will be observed with this and other embodiments described herein, the circumferentially applied radial compression of the medical device 102 (e.g., applied by the bore 218 of the spherical member 214) may, in some applications, be considered advantageous as compared to anchors that immobilize the medical device via opposing and relatively rigid (e.g., metal or plastic) engagement members.

Figure 10:
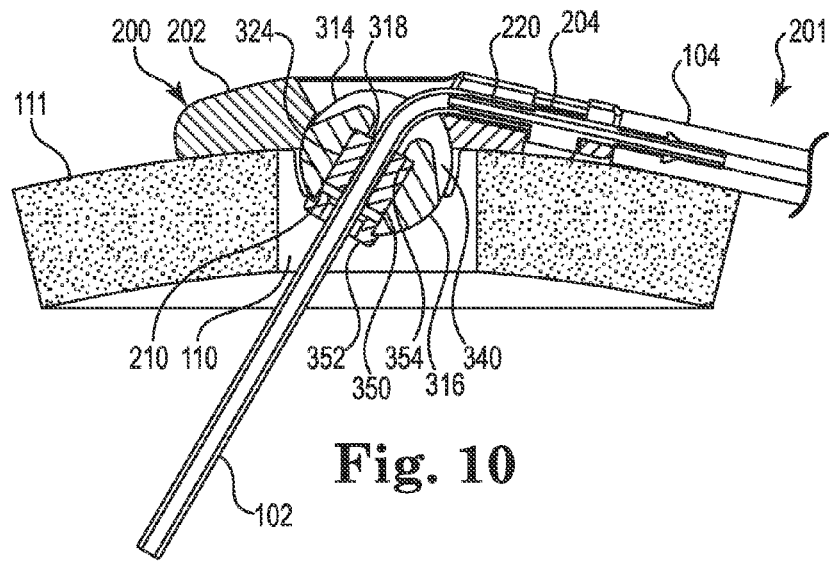
FIG. 10 is a section view similar to FIG. 5 but illustrating an anchor in accordance with another embodiment of the invention.
Figure 11:
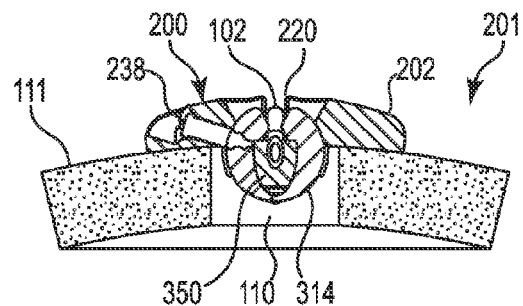
FIG. 11 is a section view like FIG. 9, but illustrating the embodiment of FIG. 10.
Figure 12:
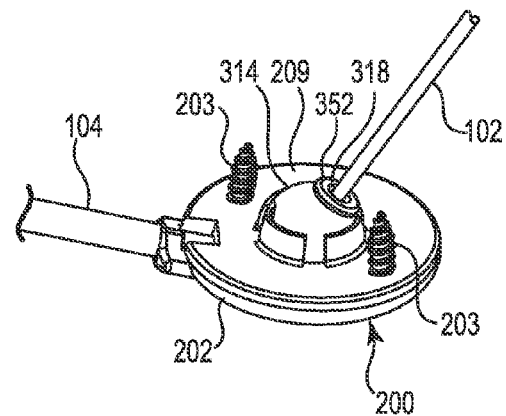
FIG. 12 is a bottom perspective view of the embodiment of FIG. 10.

FIGS. 10-12 illustrate an alternative embodiment of the anchor 200 that is, with the exception of the construction of the retention member, identical to the anchor already described herein above. For the sake of brevity, description of those aspects common to both embodiments will not be repeated herein.

As shown in FIG. 10, a retention member, e.g., spherical member 314, may replace the spherical member 214 within the anchor 200. Like the spherical member 214, the spherical member 314 is generally ball-shaped and includes a spherical surface 316 and a bore 318. The spherical member 314 could form a simple chamfer or radius 240 like the radius 240 described above. Alternatively, it could incorporate a slot or recess 340 that may intersect the bore 318 and extend away therefrom in a circumferential direction (e.g., it may extend away from one or both sides of the bore). The recess 340 could be beneficial to further ensure that the medical device 102 is not kinked or occluded by the edge of the bore 318 when the device is bent over and placed into the groove 220.

The spherical member 314 may also differ from the spherical member 214 in the construction of the bore 318. As shown in FIG. 10, the bore 318 is defined, at least in part, by a separate retaining sleeve 350 that defines a contact area 324 between the spherical member and the medical device (e.g., catheter 102) to frictionally engage the medical device. An optional sleeve cap 352 may also be included to assist with retaining the sleeve 350 within the spherical member 314.

To accommodate the sleeve 350 and cap 352, the spherical member 314 may be created with an oversized diameter to receive the sleeve. The diameter may be stepped (counterbored from below) as shown in FIG. 10 to define retaining portions, e.g., a land or stop surface 354, that assist with locating and retaining the sleeve 350. Once the sleeve 350 is located, the sleeve cap 352 may be attached at the lower end of the member 314. To ensure that the sleeve 350 and cap 352 remain in place, one or both components may be secured by any acceptable method including, but not limited to, sonic welding, interference fit, adhesive, and thermal bonding techniques.

The spherical member 314 may offer certain advantages. For example, a single spherical member 314 could accommodate sleeves (and caps) having a variety of inner diameters. As a result, one spherical member could be used with different sleeves 350 to provide for medical devices of different materials and/or diameters. Moreover, by utilizing the separate sleeve 350, a second material of the sleeve (e.g., silicone) may be optimized for frictional engagement and retention of the medical device 102, while a first material of the outer spherical surface 316 (e.g., urethane or some other material potentially different than the first material) may be optimized to interact, e.g., rotate more smoothly, with the socket 210 of the base 202 and/or resist undesirable deformation of the member 314 when penetrated by the screw 238 (see FIG. 11). FIG. 11 is a section view illustrating the spherical member 314 once the lock member (e.g., screw 238) is actuated. Moreover, FIG. 12 illustrates a bottom view illustrating the sleeve cap 352.

FIGS. 13-17 illustrate an anchor system 401 having a cranial burr hole anchor 400 in accordance with yet another embodiment of the invention. Those of skill in the art will recognize similarities between the anchor 400 and those described elsewhere herein (e.g., the anchor 200), and that components of the different embodiments described and illustrated herein may be substituted to yield yet additional embodiments without departing from the scope of the invention.

Unlike the anchor 200, the anchor 400 is described and illustrated in the context of an electrical lead 102. However, as already stated, such an application is exemplary only and the anchor 400 could be used to anchor a therapy catheter without departing from the scope of the invention.

Figure 13:
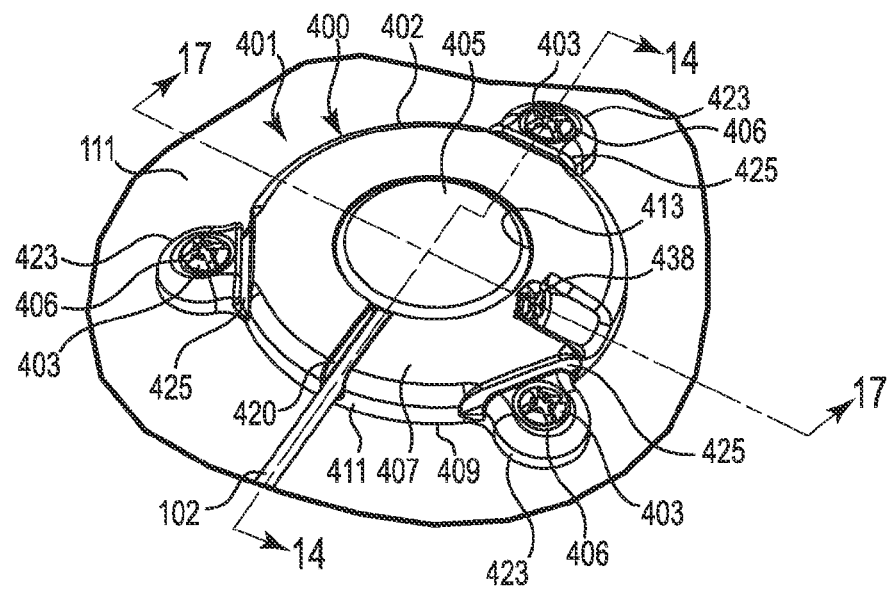
FIG. 13 is a top perspective view of an anchor in accordance with yet another embodiment of the invention.
Figure 14:
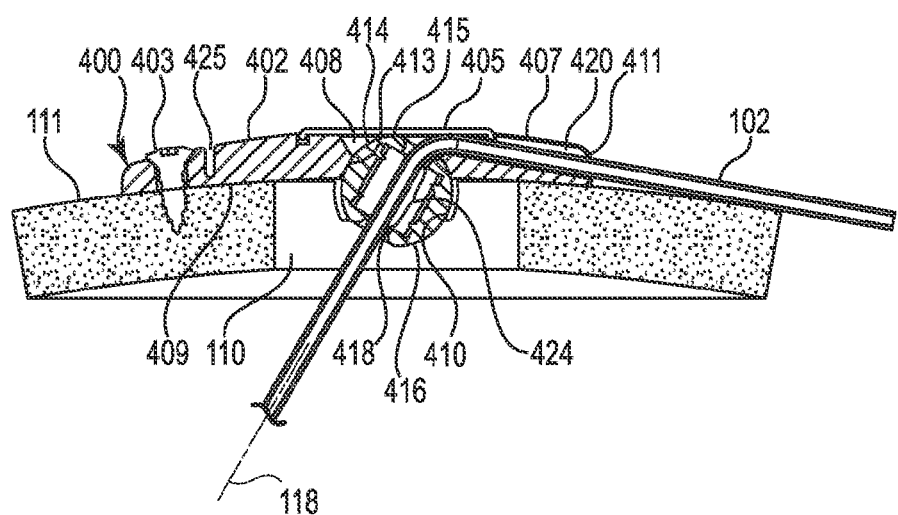
FIG. 14 is a section view taken along line 14-14 of FIG. 13.

With reference primarily to FIGS. 13 and 14, the anchor 400 may again include an annular base 402 positionable to surround the burr hole 110 (covered by the anchor in FIG. 13, but see FIG. 14). The anchor 400 (e.g., the base 402) is operable to secure to the tissue, e.g., to an outer surface of the bone (skull 111), surrounding the burr hole 110 via any acceptable method. In the illustrated embodiment, the base 402 is secured with bone screws 403 extending through openings (e.g., holes 406) formed through the base 402 and threaded into the skull 111. In the illustrated embodiment, the holes 406 are formed in portions 423 of the base 402 that protrude outwardly as shown in FIG. 13. Such a construction may benefit from flex grooves 425 that permit the portions 423 to flex as the base 402 is attached to the skull 111 with the screws 403.

Figure 16:
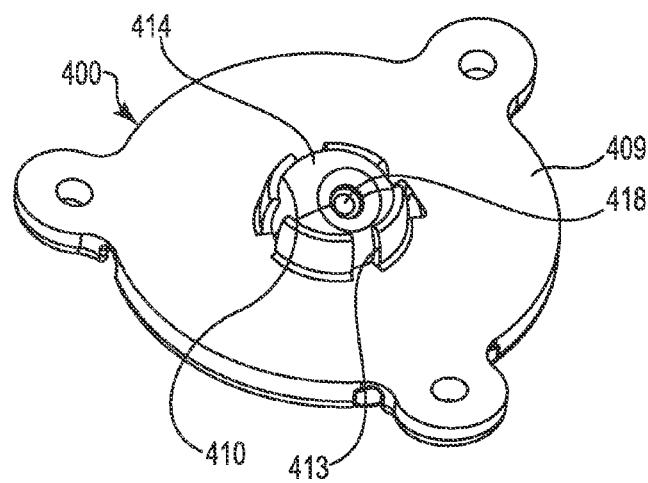
FIG. 16 is a bottom perspective view of the anchor of FIG. 13.
Figure 17:
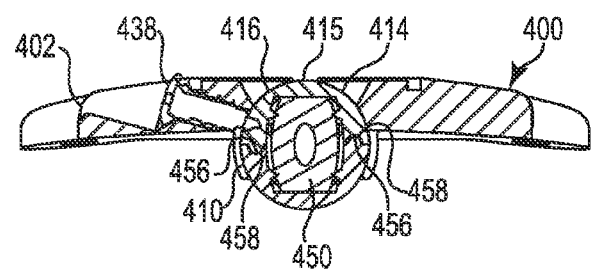
FIG. 17 is a partial section view (e.g., cap removed) taken along line 17-17 of FIG. 13.

The base 402 may include an upper side 407, a lower side 409, a peripheral or outer edge 411, and an inner edge 413. The inner edge 413 may define an opening 408 passing through the base 402 between the upper and lower sides 407 and 409, wherein the inner edge further defines a socket 410 as is also shown in FIGS. 16 and 17. An optional cap or cover 405 may attach to the base 402 to cover the opening 408 after the medical device 102 is implanted.

The socket 410 may be configured to receive therein a retention member that forms or otherwise includes a convex or spherical surface 416 (see FIG. 14). In the embodiment illustrated in FIGS. 13-17, the retention member may once again form a ball-shaped or spherical member 414. The retention member (e.g., spherical member 414) is configured to be received within the socket 410 such that the retention member is operable, under certain circumstances, to rotate therein about three mutually perpendicular axes (see, e.g., axes x, y, and z of FIG. 4).

As with the spherical members 214 and 314 described above, the spherical member 414 may include a bore 418 formed therethrough. The bore 418 is configured to permit passage of the medical device (e.g., catheter or lead 102) through the base 402 from the upper side 407 to the lower side 409. Moreover, once again, the spherical member 414 may be positioned within the socket 410 such that an uppermost surface 415 of the retention member is at an elevation at or below the upper side 407 of the base as perhaps best illustrated in FIGS. 14 and 17. Such a low profile construction may accommodate a relatively flat cover 405 as shown.

As shown in FIG. 14, the opening 408 may again be positioned to align coaxially with the burr hole 110. Moreover, the upper side 407 of the base 202 may define a passage, e.g., groove 420, extending from the inner edge 413 to and through the outer edge 411. The groove 420 may again define a passage configured to receive therein the lead 102 as shown in FIGS. 13-14. As connection to a separate device is not necessary with the lead 102, the groove 420 may be devoid of features useful to accommodate a connector like the connector 204 described elsewhere herein. The groove 420 may be configured in most any acceptable manner that provides a passage or channel extending from the opening 408 through the peripheral or outer edge 411. In the illustrated embodiment, the groove 420 is again configured as a relatively open-faced trough as shown in FIG. 13. As with the anchor 200, most any biocompatible material is suitable for the base 402 and cap 405, e.g., moldable thermoplastic (e.g., polysulfone or PEEK) or metal such as grade 2 or grade 5 Titanium.

Once again, while illustrated with the lead 102, the anchor 400 may also be applicable to a therapy catheter 102 (although connection to a delivery catheter may not be accommodated within the base 402).

Figure 15:
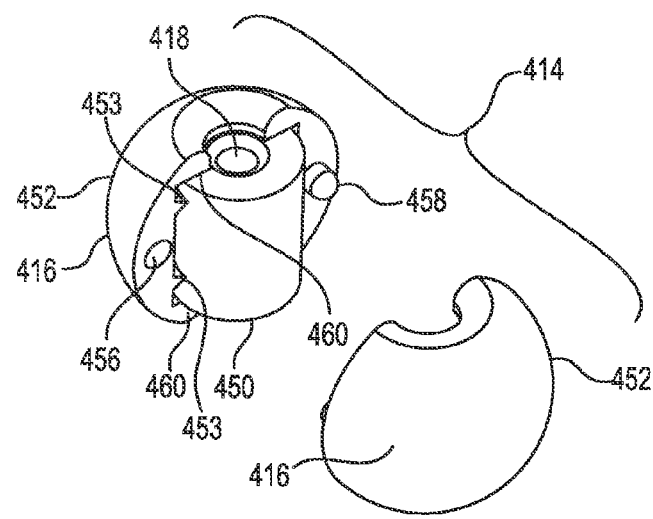
FIG. 15 is an exploded view of a retention member, e.g., spherical member, of the anchor of FIGS. 13-14.

The spherical member 414 and associated socket 410 of the base 402 function in a manner substantially similar to the spherical members 214 and 314 already described herein. However, the actual construction of the spherical member 414 may vary in comparison as illustrated in FIG. 15. As stated elsewhere herein, the spherical members described herein (e.g., 214, 314, 414, and those described subsequently), may be substituted for one another without departing from the scope of the invention.

As shown in FIG. 15, the bore 418 of the spherical member 414 is defined, at least in part, by a separate cylindrical retaining sleeve 450 that defines a contact area 424 (see FIG. 14) between the spherical member 414 and the medical device (e.g., lead 102). Unlike the spherical member 314, however, the spherical member 414 is constructed as two mating semi-spherical halves 452 that join to form a unified, ball-shaped member. To assist with aligning the halves 452, each half may include a recess 456 and a tab 458 (only one half visible in FIG. 15, but see FIG. 17). As shown in FIG. 14, the sleeve 450 (like the sleeve 350 and some of the other retention members described below) may permit the bore 418 to apply its radial compression force to the medical device 102 (e.g., frictionally receive the medical device) over a substantial portion of a length of the bore.

To accommodate and contain the sleeve 450, a passageway formed through the spherical member 414 (the two halves 452 when assembled) may be formed with an oversized diameter near its center that steps or reduces near each end of the opening. The result is an internal pocket formed within the spherical member 414 that is sized to accommodate the sleeve 450 therein as shown in FIG. 15. Lands formed by the reduced diameter near each end of the spherical member 414 form retaining portions 460 configured to receive and retain (e.g., axially) the sleeve 450 within the spherical member 414. Alternatively, the sleeve 450 could be secured by other methods including, but not limited to, sonic welding, interference fit, adhesive, and thermal bonding techniques. As shown in FIG. 15, teeth 453 may hold the sleeve 450 near the center of the bore while still allowing the sleeve to expand, e.g., when the guide cannula (described below) is inserted.

Once assembled, the spherical member 414 may be pressed into the socket 410 of the base 402 such that it is restrained from all but rotation about the three mutually perpendicular axes (see FIG. 4). The anchor 400 is then ready for use in a manner similar to that already described above. FIG. 16 illustrates a bottom perspective view of the anchor 400 illustrating the spherical member 414 assembled and located within the socket 410, while FIG. 17 illustrates a cross-sectional view of the anchor 400 after the lead 102 trajectory is fixed. In a manner similar to the anchor 200, the anchor 400 may include a lock member (e.g., screw 438) to lock or immobilize the spherical member 414 relative to the base 402 as shown.

By utilizing a different component/material for the device contact area 424 and the spherical surface 416, the spherical member 414 may offer advantages similar to those already described with respect to the member 314 (e.g., a single spherical member could accommodate multiple sleeves (and thus multiple medical devices) of different materials and/or diameters; different materials may be utilized for the sleeve versus the spherical surface 416).

FIGS. 18-23 illustrate an exemplary surgical lead implant procedure that may be used with the anchor 400 described above. However, it is noted that the anchor 400 and lead are illustrative only as the method is generally applicable to the implantation of either a catheter or lead using any of the anchor embodiments described herein (i.e., the method would be similar for implantation using the anchor 200).

Figure 18:
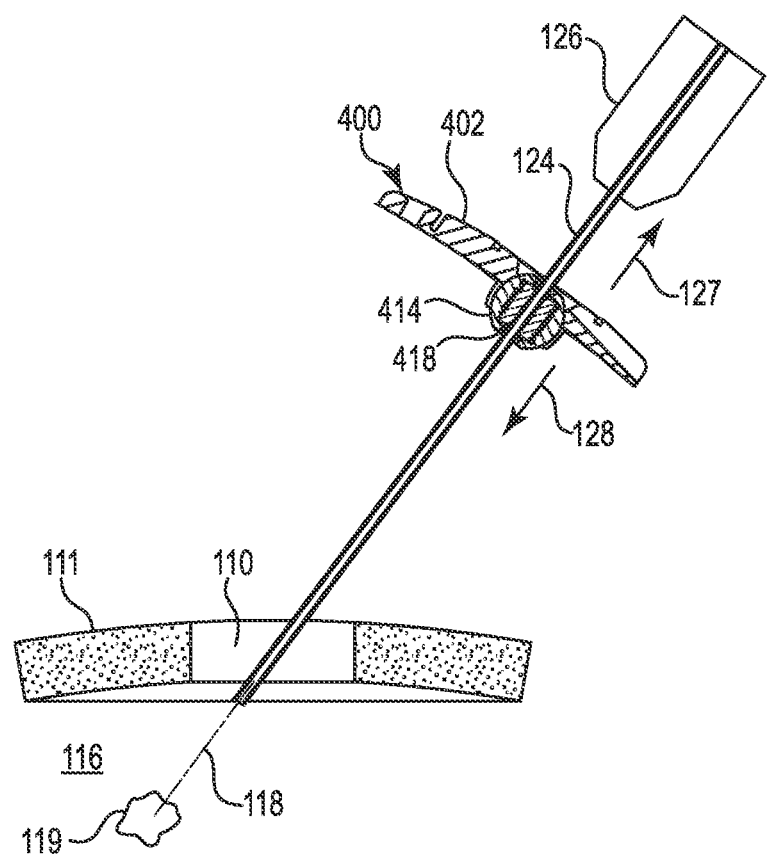

After forming the burr hole 110 in the skull 111, a guide cannula 124 may be attached to a headframe guide adapter 126 of the stereotactic apparatus 103 (see FIG. 1). The stereotactic apparatus 103 may then be configured such that the guide cannula 124 aligns with the burr hole 110 and the target tissue location 119 within the brain 116. That is, the guide cannula 124 may be configured such that its axis (i.e., the intended medical device trajectory 118) intersects with the target tissue location 119 as shown in FIG. 18. The anchor 400 (or 200) may then be slid over a distal end of the guide cannula 124 (i.e., the distal tip may be inserted through the bore 418 of the spherical member 414) and slid upwardly (e.g., in the direction 127) toward the guide adapter 126 before the distal end of the guide cannula is inserted into the burr hole 110. The guide cannula 124 may then be advanced until the distal end of the guide cannula is inside the burr hole and at or near a surface of the dura as shown in FIG. 18.

Regardless of the configuration of the spherical member (e.g., regardless of whether the member 214, 314, or 414 is used), the bore is configured to expand/deform sufficiently to permit sliding entry of the guide cannula 124. The friction between the bore of the spherical member and the guide cannula 124 is preferably sufficient to provide some resistance to unintended gravitational sliding of the anchor toward the burr hole.

Figure 19:
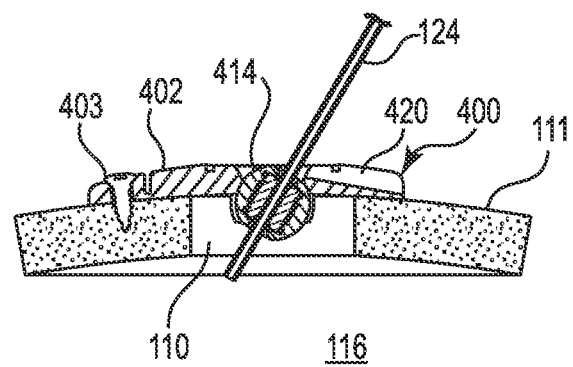

At this point, the surgeon may slide the anchor 400 (or 200) down the guide cannula 124 toward the skull 111 surface as represented by directional arrow 128. The base 402 may then be rotated about the spherical member 414 until the base sits flush to the tissue (skull 111) surface as shown in FIG. 19.

In instances where the spherical member includes a recess on its spherical surface (e.g., a recess 340 as provided with the spherical member 314), the base (e.g., 302) and/or spherical member (e.g., 314) may also be rotated about the spherical member until the recess aligns with the groove (e.g., groove 220) formed in the base (e.g., base 202).

Figure 20:
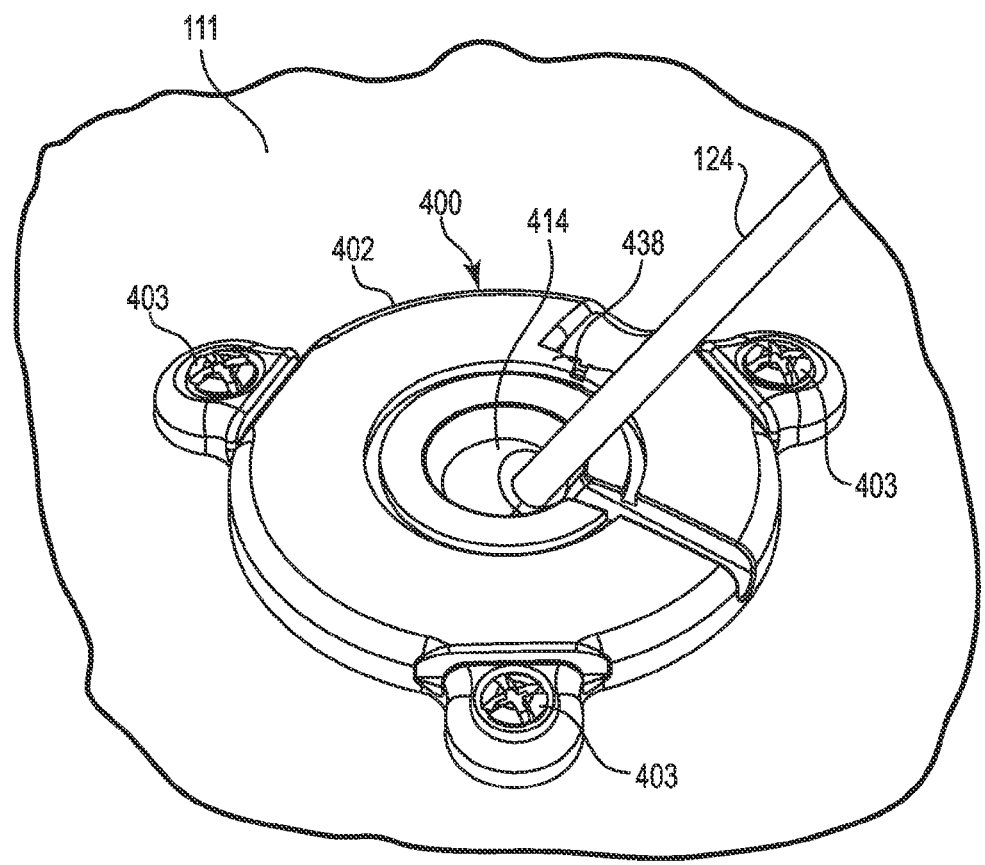
Figure 21:
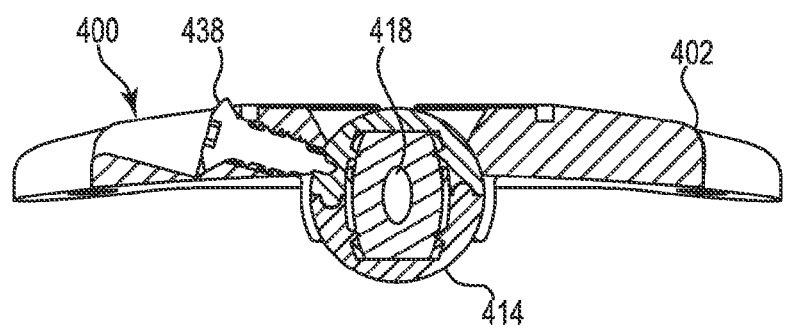

Once the base is flush to the skull, the base may be secured to tissue, e.g., using the bone screws 403 (or 203) as shown in FIG. 20. At this point, the spherical member (e.g., member 214, 314, or 414) may be locked or immobilized relative to the base (e.g., base 202 or 402) using the lock member (e.g., screw 238 or 438). That is, the screw may be turned until it threadably penetrates (e.g., self-taps) the spherical member and locks the latter relative to the base as shown in FIG. 21. The anchor is then locked such that the bore (e.g., bore 418) is coincident with the trajectory 118.

Figure 22:
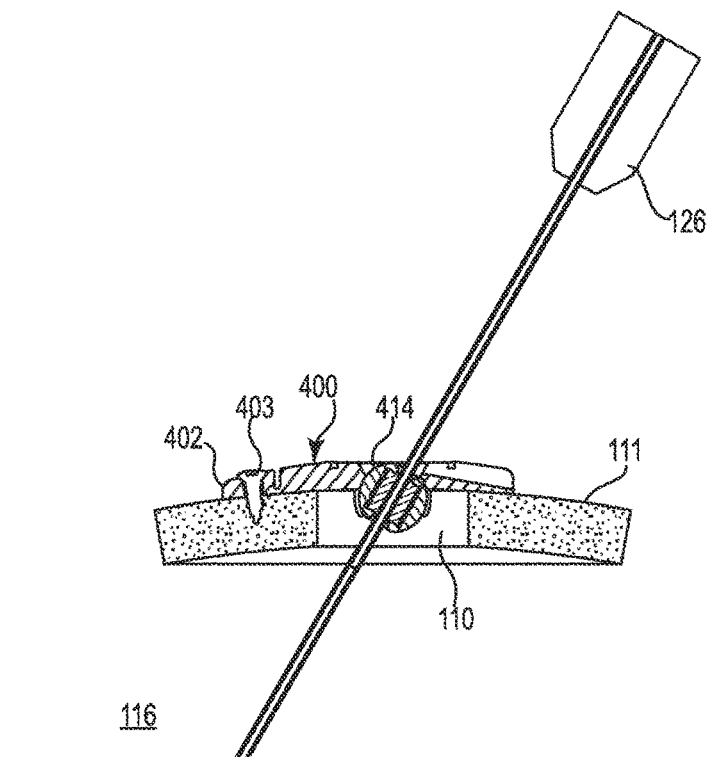

The guide cannula 124 may then be advanced until its distal end is at or near the target tissue location 119 as shown in FIG. 22. The lead 102 (or catheter) may then be inserted into the guide cannula 124 in accordance with known techniques until the therapy delivery tip 108 of the device 102 is at the target tissue location 119.

Figure 23:
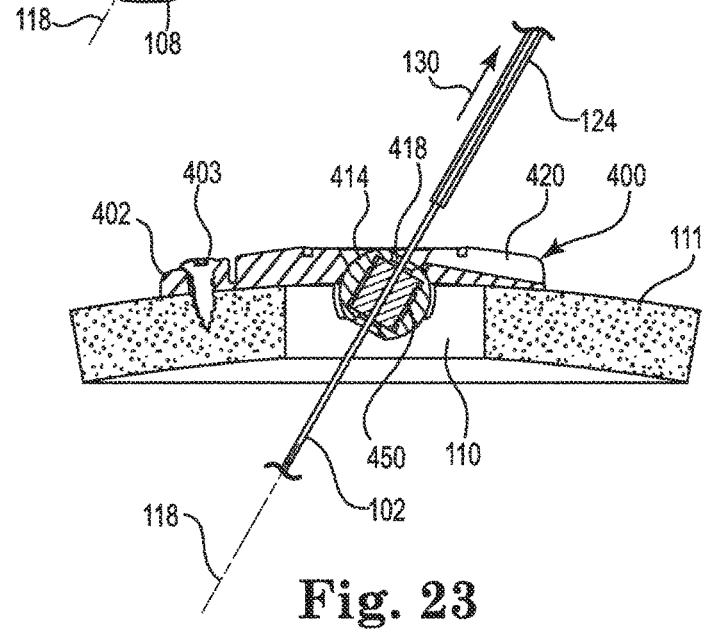

When the medical device has been positioned, the guide cannula 124 may be withdrawn or retracted (moved in the direction 130) as shown in FIG. 23 while holding the device 102 in place, e.g., with a stylet (not shown) and the stereotactic apparatus 103 (see FIG. 1). As the guide cannula 124 retracts beyond the bore (e.g., beyond the sleeve 450 of the bore 418 of the spherical member 414), the elastomeric properties of the spherical member/bore immediately contract to compress against the outer diameter of the medical device 102 as indicated in FIG. 23. That is, the securing of the medical device 102 along the trajectory 118 is immediate and automatic upon cannula withdrawal. Moreover, the resulting compression (radial) retention force applied to the medical device 102 is sufficient to secure the medical device relative to the anchor 200 while the device is implanted.

In the illustrated embodiment, the bore of the spherical member may expand sufficiently to accept the guide cannula 124 (which may, in one embodiment, be about 1.7 mm in diameter), and then immediately contract to contact and immobilize the medical device 102 (which may, in one embodiment, be about 1 to 1.3 mm). As a result, the frictional compression force applied against the guide cannula by the spherical member may be substantially higher that that provided to the medical device. In one embodiment, a lubricous coating, such as polytetrafluoroethylene (PTFE), may be applied to the guide cannula 124 to permit insertion/withdrawal of the cannula from the spherical member.

In the case of the lead 102 (or direct connection of the therapy catheter to the therapeutic source), the guide cannula may next be separated entirely from the lead, after which the lead may be bent (after stylet removal) until it lies within the groove 420 as shown in FIGS. 13 and 14 or is otherwise adjacent to the upper side of the base. The optional cap 405 may then be attached to the base 402 (see FIG. 13) and the lead (or therapy catheter) attached to the therapy source 106 (see FIG. 1).

Alternatively, in the case of catheter implantation, the catheter may be cut (e.g., about 25 mm) above the anchor 200 after stylet removal. With reference to FIG. 4, the catheter 102 may then be folded over and placed into the groove 220 where a final cut may be made at or near the relief 222. The first end 226 of the connector 204 may then be manually inserted by the surgeon into the lumen of the cut therapy catheter 102. The connector 204 may then be pressed into the groove 220 until it locks in place with a snap-fit. The delivery catheter 104 may then be connected to the second end 228 of the connector 204 as shown in FIG. 4.

FIGS. 24-28 illustrate an infusion system incorporating an anchor system 501 having a cranial burr hole anchor 500 in accordance with still yet another embodiment of the invention. Once again, those of skill in the art will recognize similarities between the anchor 500 and those described elsewhere herein (e.g., the anchors 200 and 400), and that various components of the different embodiments described and illustrated herein could be substituted among one another to yield yet additional embodiments without departing from the scope of the invention.

Figure 24:
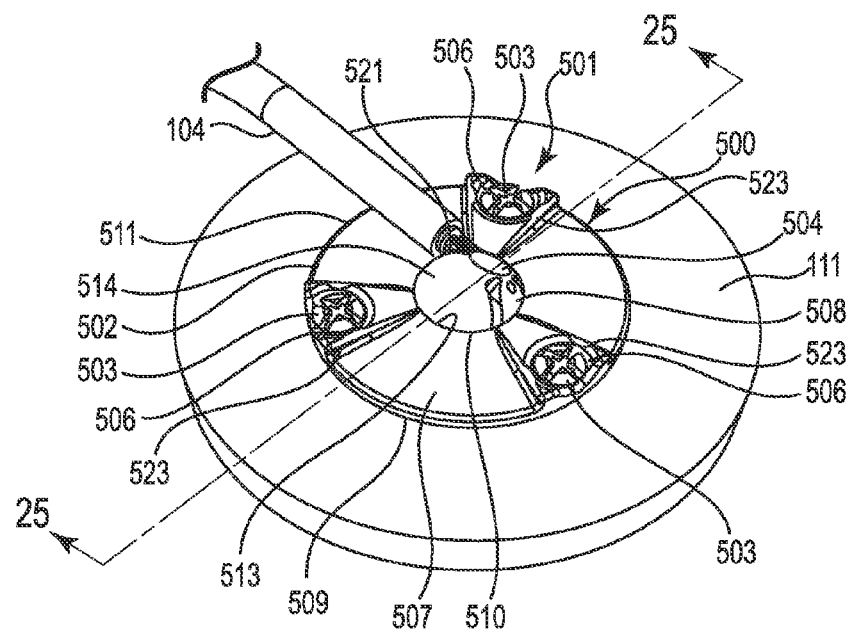
FIG. 24 illustrates an anchor in accordance with still another embodiment of the invention.
Figure 25:
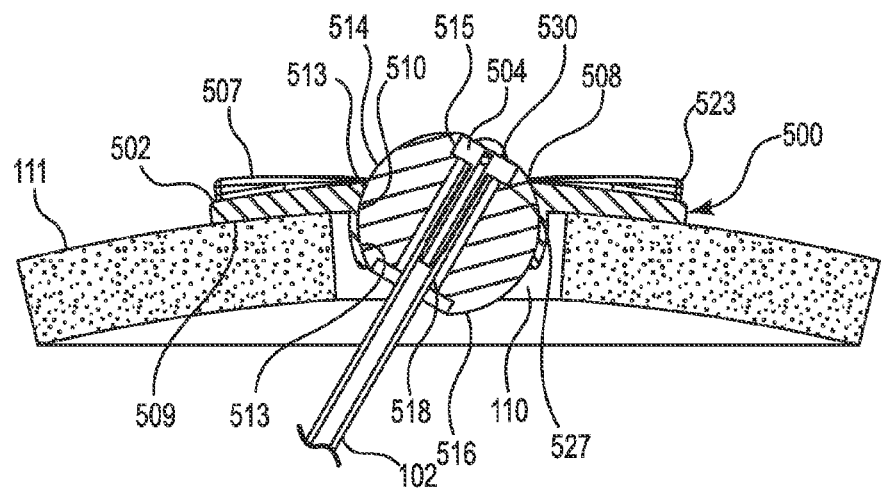
FIG. 25 illustrates a section view taken along line 25-25 of FIG. 24.

The anchor 500 may be designed specifically for use in anchoring a therapy catheter 102 rather than a lead. With reference primarily to FIGS. 24 and 25, the anchor 500 may again include an annular base 502 that may be positioned to surround the burr hole 110 (covered by the anchor in FIG. 24, but see FIG. 25). The anchor 500 (e.g., the base 502) is operable to secure to the tissue, e.g., to an outer surface of the bone (skull 111), surrounding the burr hole 110 via any acceptable method. In the illustrated embodiment, the base 502 is secured with bone screws 503 extending through openings (e.g., holes 506) formed through the base 502 and threaded into the skull 111. The holes 506 may be formed in portions 523 of the base 502 that protrude upwardly relative to the remainder of the base as shown. Such a construction may provide advantages as further described below.

The base 502 may include an upper side 507, a lower side 509, a peripheral or outer edge 511, and an inner edge 513. The inner edge 513 may define an opening 508 passing through the base 502 between the upper and lower sides 507 and 509, wherein the inner edge further defines a socket 510. The socket 510 may be configured to receive therein a retention member that forms or otherwise includes a convex or spherical surface 516 (see FIG. 25). In the embodiment illustrated in FIGS. 24-28, the retention member may, once again, form a ball-shaped or spherical member 514. The retention member (e.g., spherical member 514) is configured to be received within the socket 510 such that the retention member is operable, under certain circumstances, to rotate therein about three mutually perpendicular axes (see, e.g., axes x, y, and z of FIG. 4).

As with the spherical members 214, 314, and 414 described above, the spherical member 514 may include a bore 518. The bore 518 is configured to permit passage of the therapy catheter 102 through the base 502 from the upper side 507 to the lower side 509 as shown in FIG. 25. While the illustrated embodiment incorporates a low-profile base 502 such that an uppermost surface 515 of the spherical member 514 protrudes above the base (see FIG. 25), such a configuration is not limiting. For example, the base 502 could be configured with greater depth (or the spherical member 514 could seat lower in the base) such that the uppermost surface 515 is at an elevation at or below the upper side 507.

As shown in FIG. 25, the opening 508 may again be positioned to align coaxially with the burr hole 110. Moreover, the anchor 500 may also include a connector 504 that, like the connectors 204 and 404 described herein, may permit fluid connection between the therapy catheter 102 and the delivery catheter 104 as further described below. However, unlike the connectors 204 and 404, the connector 504 may locate directly to the retention member 514, e.g., in the bore 518. As a result, there is no need to accommodate the connector 504 or the delivery catheter 104 via a groove on the upper side 507 of the base 502 (e.g., any groove equivalent to the grooves 220, 420 may be optional on the base 502).

Suitable biocompatible materials for the base 502, spherical member 514, and connector 504 may be similar to the like components already described herein above with respect to the anchor 200.

The spherical member 514 may be pressed into the socket 510 of the base 502 such that it is restrained from all but rotation about the three mutually perpendicular axes (see, e.g., x, y, and z axes of FIG. 4). The spherical member 514 (as well as the base 502) may thus function in a manner similar to the spherical members 214, 314, and 414 already described herein. However, the actual construction of the spherical member 514 may differ to accommodate the connector 504 as further described below. One of skill in the art will, once again, realize that aspects of the various spherical members (e.g., 214, 314, 414, 514, and those described below) may be substituted for one another without departing from the scope of the invention.

As shown in FIG. 25, the bore 518 is formed through the spherical member 514 and is sized, in one embodiment, such that the therapy catheter 102 is received therein with clearance or minimal interference. That is, in one embodiment, the bore 518 does not compressively engage the catheter.

Figure 26:
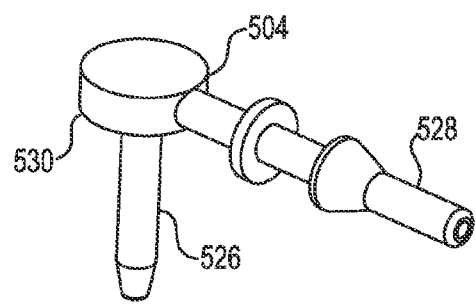
FIG. 26 is a perspective view of a connector for use with the anchor of FIG. 24.

As shown in FIG. 26, the connector 504 may form a right angle member connecting the therapy catheter 102 to the delivery catheter 104. As such, it includes a first end 526 defining a therapy tip, and an opposite or second end 528 defining a delivery tip. A longitudinal axis defined by the first end is, in the illustrated embodiment, normal to a longitudinal axis defined by the second end as shown. The connector 504 may further include an enlarged central portion 530 between the first and second ends. The first and second ends 526,528 (e.g., the therapy tip and the delivery tip) may be configured for insertion into lumens of, respectively, the therapy catheter 102 and the delivery catheter 104. The shape and size of the first and second ends of the connector 504, as well as the size and material of the catheters, may be selected to produce a relatively secure and leak-free connection between the catheters and the connector when joined. As with the connector 204, the connector 504 is hollow to permit passage of fluid from the delivery catheter 104 to the therapy catheter 102.

The central portion 530 of the connector 504 may be sized to be received within the bore of the spherical member 514 such that the connector seats within the spherical member. That is (as further described below), the first end 526 of the connector 504 may be inserted into the bore 518 and pushed (downwardly in FIG. 25) until the central portion 530 seats against a stop surface of a counterbore or relief 527 formed in the bore. As the first end 526 of the connector 504 enters the bore 518, it may slide into the lumen of the therapy catheter 102 as shown in FIG. 25. As further described below, the spherical member 514 may include engagement tabs 521 (see FIG. 24) that securely receive the second end 528 of the connector 504 (e.g., with a snap-fit) once the first end 526 and central portion 530 are fully engaged with the bore 518. Once the connector 504 is received in this manner, it is immobilized, relative to the spherical member 514. The anchor 500 provides the additional advantage in that it aligns the connector 504 (e.g., first end 526) with the catheter trajectory 118, further reducing or eliminating biasing forces on the therapy catheter 102 in a lateral direction.

Figure 27:
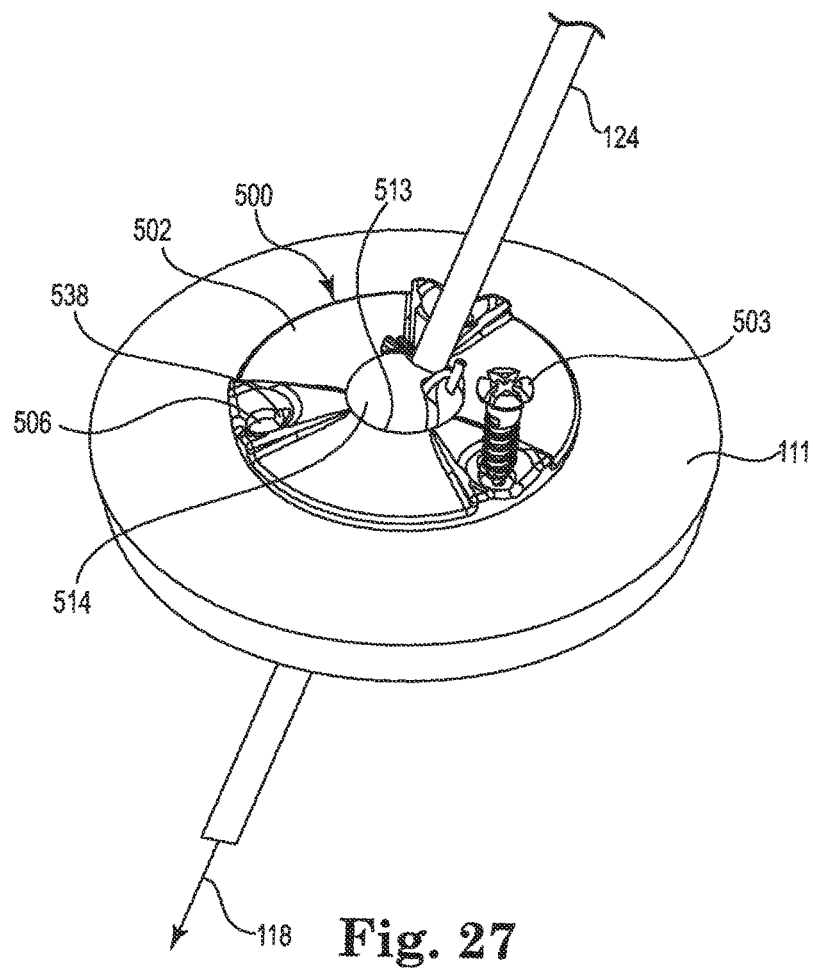
FIG. 27 is a perspective view illustrating the anchor of FIG. 24 before immobilization of a retention member of the anchor.
Figure 28:
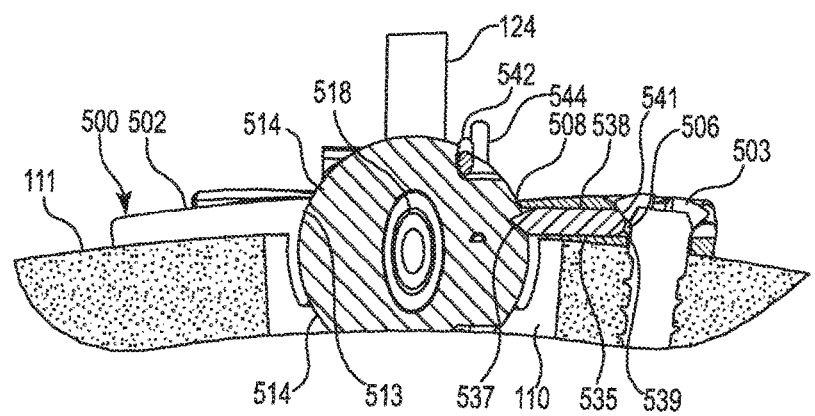
FIG. 28 is a section view illustrating the anchor of FIG. 24 after immobilization of the retention member.

As with the anchors described elsewhere herein, the retention member 514 may be immobilized relative to the base 502 using one or more lock members, an example of which is illustrated in FIGS. 27 and 28 (although lock members such as those already described herein may certainly be used with the anchor 500). Unlike the anchors 200 and 400, the anchor 500 may incorporate a lock pin 538 associated with one or more of the bone screws 503. The lock pins 538 may be located within a passageway 535 that extends from the holes 506 of the base 502 to the opening 508 (e.g., through the inner edge 513). Each lock pin 538 may include a pin end 537 configured to selectively protrude from the base into the socket 510 and penetrate the spherical member 514 to lock the spherical member relative to the base 502. To activate the lock pin 538, an engagement end 539 of the lock pin may protrude into the opening 506. As the bone screw 503 associated with the opening 506 is tightened, a bevel 541 formed on the screw contacts the engagement end 539 of the lock pin and translates the lock pin along the passageway 535 towards the spherical member 514. The lock pin 538 and bevel 541 may be configured to ensure that, once the bone screw 503 is fully tightened, the pin end 537 has penetrated the spherical member 514 adequately to lock the spherical member in place, but does not penetrate into the bore 518. Those of skill in the art will realize that this pin locking mechanism may be utilized with other anchor base embodiments (e.g., anchors 200 and 400) described herein.

With reference to FIGS. 29-34, an exemplary surgical catheter implant procedure using the anchor 500 is now described. After forming the burr hole 110 in the skull 111, a guide cannula 124 may be attached to a headframe guide adapter (see, e.g., headframe adapter 126 of stereotactic apparatus 103 in FIG. 18 already described herein), wherein the stereotactic apparatus 103 may be configured such that the guide cannula 124 aligns with the target tissue location 119 within the brain 116. That is, the guide cannula 124 may be configured such that its axis (i.e., the intended medical device trajectory 118) intersects with the target tissue location 119 as shown in FIG. 18. The anchor 500 may then be slid over a distal end of the guide cannula 124 (i.e., the distal end may be inserted through the bore 518 of the spherical member 514) and slid towards the guide adapter 126 before the distal end of the guide cannula is inserted into the burr hole 110. The guide cannula 124 may then be advanced until the distal end of the guide cannula is at or near a surface of the dura (see, e.g., FIG. 18).

Figure 29:
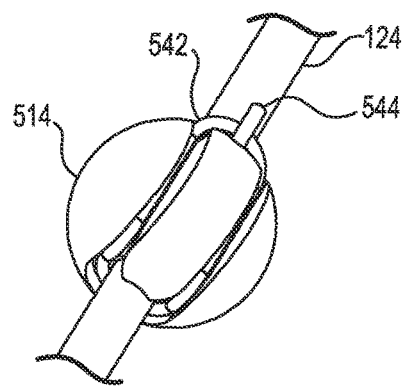

Prior to advancing the guide cannula 124 to the dura, the surgeon may engage an elastomeric member, e.g., O-ring 542, such that it stretches to extend around the guide cannula 124 on the lower side of the spherical member 514 and connects to a retaining pin 544 secured to a top side of the spherical member as shown in FIG. 29. The spherical member 514 may define a series of grooves to accommodate the O-ring 542 as shown in FIG. 29 (note that remainder of anchor is removed in FIG. 29 to better illustrate the O-ring and its routing). The O-ring 542 may provide sufficient tension to hold the guide cannula 124 against a side of the bore 518 of the spherical member 514, while still permitting relative sliding movement of the guide cannula relative to the bore.

The surgeon may then slide the anchor 500 down the guide cannula 124 until the anchor seats on the skull 111 surface (see, e.g., FIG. 19). Once the base 502 is flush to the skull, the base may be secured to tissue, e.g., to the skull 111, using the bone screws 503. As described above, the bone screws not only secure the base to the tissue (skull 111), they also actuate the lock pins 538 (see FIG. 28) as already described herein to immobilize the spherical member 514 relative to the base 502. That is, tightening of the bones screws 503 causes each lock pin 538 to penetrate the spherical member 514 and immobilize the latter relative to the base 502 such that the bore 518 is aligned with the trajectory 118.

The guide cannula 124 may then be advanced until the distal end is at or near the target tissue location 119 as already described herein (see, e.g., FIG. 22). The therapy catheter 102 may then be inserted into the guide cannula 124 in accordance with known techniques until the delivery tip 108 of the therapy catheter is at the target tissue location 119.

Figure 30:
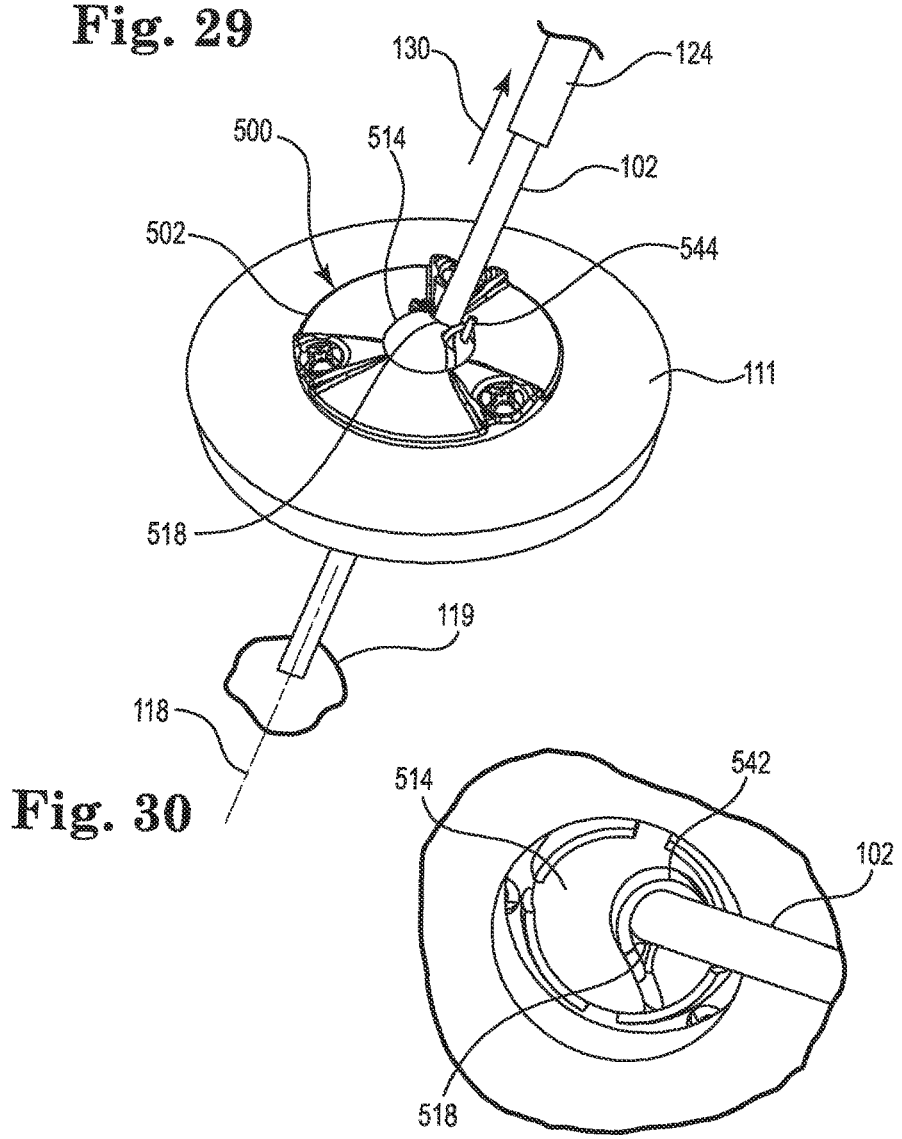
Figure 31:
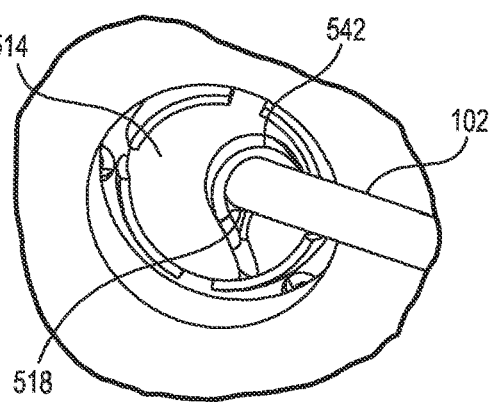

When the therapy catheter 102 has been positioned, the guide cannula 124 may be retracted (moved in the direction 130) as shown in FIG. 30 while holding the catheter in place, e.g., with a stylet (not shown) and the stereotactic apparatus 103 (see FIG. 1). As the guide cannula 124 retracts beyond the O-ring 542, the elastomeric properties of the O-ring cause it to immediately contract to pull the catheter 102 against the bore 518 as indicated in FIG. 31. The force applied to the catheter 102 by the O-ring 542 is again sufficient to secure the catheter relative to the anchor 500 during the remainder of the surgical procedure.

Figure 32:
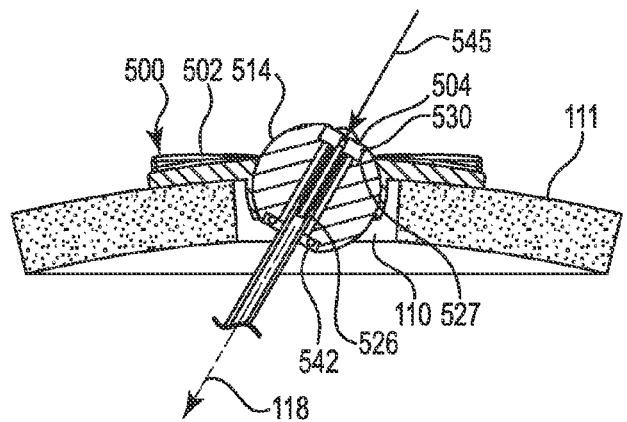
Figure 33:
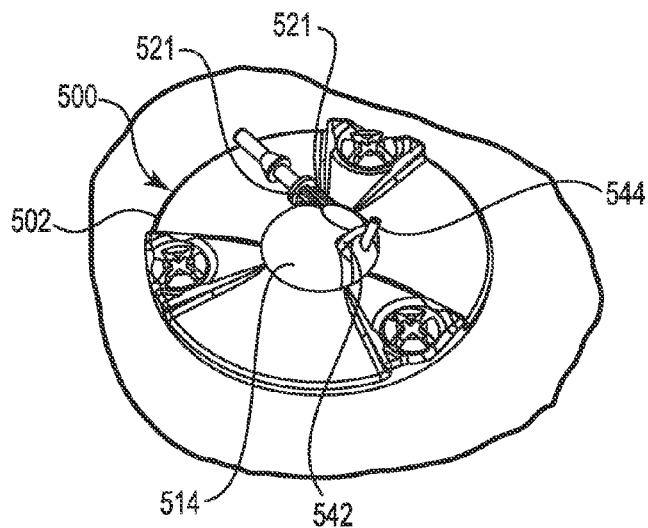

With the catheter 102 retained in the spherical member 514, the portion of the catheter protruding outwardly beyond the relief 527 (see FIG. 25) may be trimmed. The first end 526 of the connector 504 may then be inserted from above (e.g., in the direction 545), by the surgeon into the bore 518 where it ultimately enters the lumen of the now-trimmed first end of the catheter as shown in FIG. 32 (the O-ring 542 may hold the catheter 102 in place during connector 504 insertion). Once completely inserted, the central portion 530 of the connector 504 may seat within the relief 527 of the spherical member 514 as also shown in FIG. 32. Moreover, at the same time, the second end 528 of the connector 504 may engage, e.g., with a snap-fit, the engagement tabs 521 formed on the spherical member 514 as shown in FIG. 33. As a result, the catheter 102 and the connector 104 are secured relative to the spherical member 514, which is, in turn, secured to the base 502 by the lock pins 538 (e.g., see FIG. 28).

Figure 34:
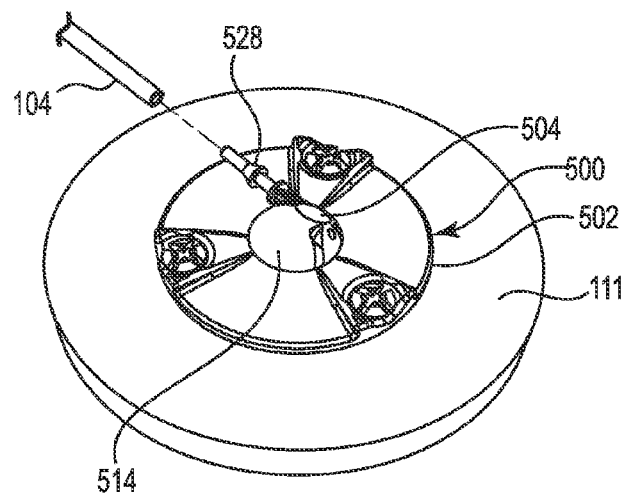

At this point, the O-ring 542 may be cut and the O-ring and retaining pin 544 removed as shown in FIG. 34. The delivery catheter 104 may then be attached to the second end 528 of the connector 504 as shown. Before or after attachment of the delivery catheter 104, the opposite end of the delivery catheter may be tunneled and connected to the therapeutic source, e.g., implantable pump 106 as shown in FIG. 1.

Figure 35:
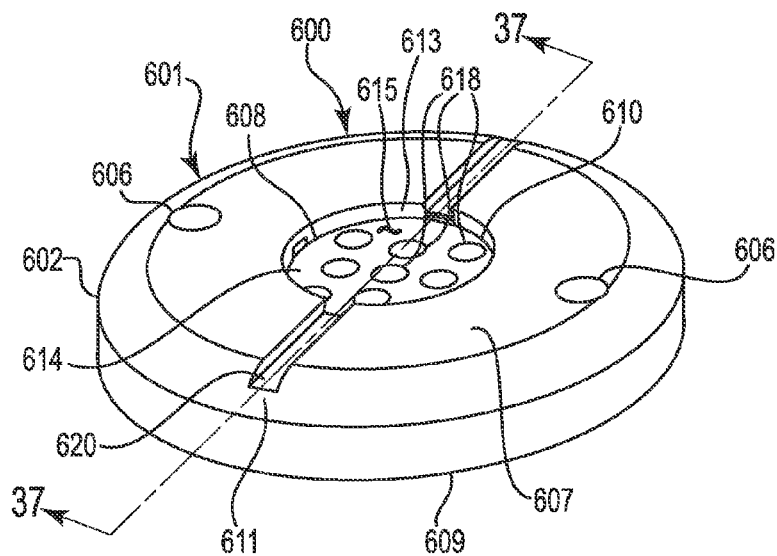
FIG. 35 illustrates an anchor in accordance with still yet another embodiment of the invention.
Figure 36:
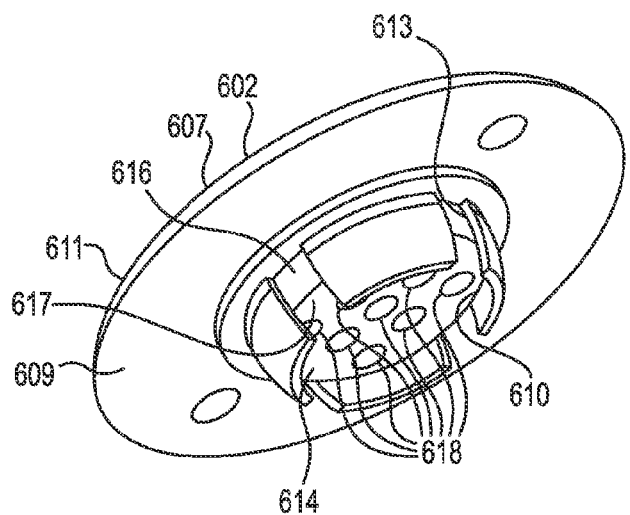
FIG. 36 is a bottom perspective view of the anchor of FIG. 35.
Figure 37:
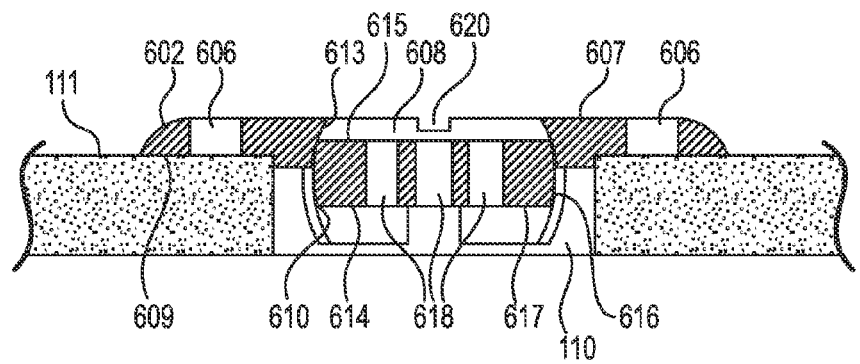
FIG. 37 is a section view taken along line 37-37 of FIG. 35.

FIGS. 35-37 illustrate an anchor system 601 having an anchor 600 in accordance with yet another embodiment of the invention. Once again, the anchor 600 may include an annular base 602 that may be positioned to surround the burr hole 110 (see FIG. 37). The anchor 600 (e.g., the base 602) is operable to secure to the tissue, e.g., to an outer surface of the skull 111, surrounding the burr hole 110, via any acceptable method. In the illustrated embodiment, the base 602 is secured with bone screws (not shown) extending through openings (e.g., holes 606) formed through the base 602 and threaded into the skull 111.

The base 602 may include an upper side 607, a lower side 609, a peripheral or outer edge 611, and an inner edge 613. The inner edge 613 may define an opening 608 passing through the base 602 between the upper and lower sides 607 and 609, wherein the inner edge further defines a socket 610. The opening 608 may again be positioned to align coaxially with the burr hole 110. While not shown, an optional cap or cover may attach to the upper side 607 of the base 602 to cover the opening 608 after the medical device 102 is implanted.

The socket 610 may be configured to receive therein a retention member 614 that forms or otherwise includes a convex or spherical surface 616. The retention member 614 is configured to be received within the socket 610 such that the retention member is operable, under certain circumstances, to rotate therein about three mutually perpendicular axes (see, e.g., axes x, y, and z of FIG. 4) as already described herein. As with the anchor 200, most any biocompatible material is suitable for the base 602, e.g., moldable thermoplastic (e.g., polysulfone or PEEK) or metal such as grade 2 or grade 5 Titanium.

The retention member 614 (as well as the base 602) may function in a manner substantially identical to the spherical members 214, 314, 414, and 514 already described herein. However, the actual construction of the retention member 614 may differ somewhat from the other retention members described herein in that the member 614 forms a truncated sphere. That is, the retention member 614 is truncated in that it has an uppermost surface 615 (when oriented as shown) forming a planar surface and, in one embodiment, a flat and parallel lower surface 617 as shown in FIGS. 36 and 37. However, as the retention member 614 has substantially spherical surfaces 616 that engage the socket 610 in a manner similar to the other retention members described herein, the truncated retention member can also be said to form a spherical member. In fact, aspects of the various spherical members 214, 314, 414, and 514, may be substituted with the spherical member 614, and vice versa, without departing from the scope of the invention.

As with the spherical members 214, 314, 414, and 514 described above, the spherical member 614 may include a bore 618 formed therethrough. The bore 618 is configured to permit passage of the medical device (e.g., catheter or lead 102, not shown) through the base 602 from the upper side 607 to the lower side 609. Moreover, the spherical member 614 may be positioned within the socket 610 such that the flat upper surface 615 of the spherical member is at an elevation at or below the upper side 607 of the base as best seen in FIG. 37. Such a low-profile construction may better accommodate a relatively flat cover (not shown) if desired.

Because the spherical member 614 incorporates the parallel planar surfaces 615, 617, it may accommodate two or more bores 618. For example, in the illustrated embodiment, the retention member 614 may include an array of nine bores arranged in a three-by-three square. The bores (i.e., longitudinal axes of the bores) may be parallel to one another and each may extend from the upper surface 615 through the lower surface 617. By providing multiple bores 618, the surgeon may have more options for catheter placement through the burr hole 110. For example, it may be beneficial to provide bores laterally spaced from the geometric center of the spherical member to allow the medical device to be located off-center in the burr hole. Such flexibility is provided in addition to the trajectory-matching spherical movement already described herein above with respect to the previously described embodiments (although it is noted that the benefit of selecting one of the outermost bores 618 may be somewhat offset by the reduced angular flexibility afforded in device trajectory).

While shown with a square array of bores 618, such a configuration is not limiting. For example, in an alternative embodiment, the spherical member 614 may have a group of bores extending across a diameter of the spherical member. In this instance, the spherical member 614 may be rotated until one of the bores 618 is in the desired catheter or lead location. Moreover, while the bores 618 are illustrated as being normal to the surface 615, one or more of the bores could, alternatively, be angled relative to the surface 615.

In most other respects, the anchor 600 may operate in a manner similar to the other anchors already described herein. For example, the upper side 607 of the base 602 may define a passage, e.g., groove 620 (see FIG. 35), extending from the inner edge 613 to and through the outer edge 611. The groove 620 may define a passage configured to receive therein the medical device (e.g., catheter 102) as already described herein. Moreover, the spherical member 614 may be immobilized relative to the base 602 via a lock member (e.g., screw 238 (not shown) as already described above with reference to the anchor 200) or, alternatively, the anchor 600 could be configured to provide sufficient friction between the socket 610 and the spherical member to effectively immobilize the latter during surgery and subsequent device implantation. Similarly, the bores 618 could be sized, and/or the material of the spherical member 614 selected, to provide the desired frictional engagement to effectively immobilize the catheter 102 relative to the retention member. Potential materials for the spherical member 614 include silicone, urethane, and the like.

An exemplary surgical procedure using the anchor 600 is evident from the procedures already described herein with regard to anchor 400 (see e.g., FIGS. 18-23). Accordingly, no further description is provided.

FIGS. 38-42 illustrate an anchor system 701 including an anchor 700 in accordance with still yet another embodiment of the invention. Those of skill in the art will recognize similarities between the anchor 700 and those described elsewhere herein, and that components of the embodiments described and illustrated herein may again be substituted among the various embodiments to yield yet other embodiments without departing from the scope of the invention.

The anchor 700 is described and illustrated in the context of an anchor for an electrical lead 102. However, as with other embodiments described herein, such an application is exemplary only, e.g., the anchor 700 could also be used to anchor a therapy catheter 102 (see, e.g., FIGS. 56 and 57).

Figure 38:
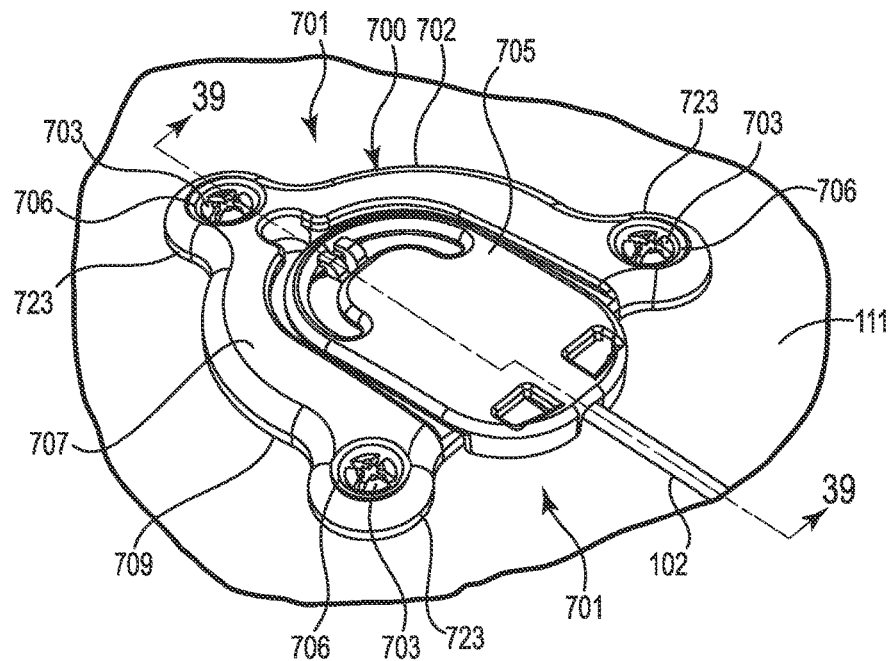
FIG. 38 is an upper perspective view of an anchor in accordance with yet still another embodiment of the invention.
Figure 39:
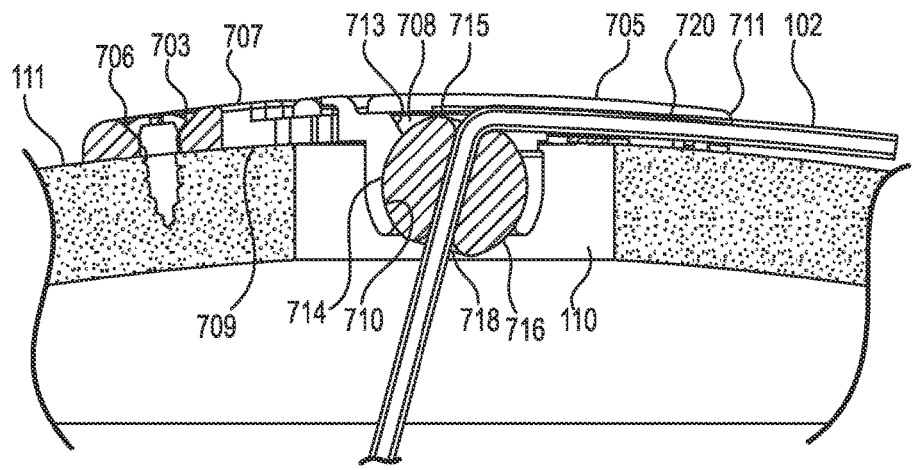
FIG. 39 is a section view taken along line 39-39 of FIG. 38.

The anchor 700 may include an annular base 702 that may be positioned to surround the burr hole 110 (covered by the anchor in FIG. 38, but see FIG. 39). The anchor 700 (e.g., the base 702) is operable to secure to the tissue, e.g., to an outer surface of the bone (skull 111), surrounding the burr hole 110 via any acceptable method. In the illustrated embodiment, the base 702 is secured with bone screws 703 extending through openings (e.g., holes 706) formed through the base 702 and threaded into the skull 111. In the illustrated embodiment, the holes 706 are formed in portions 723 of the base 702 that protrude outwardly as shown in FIG. 38.

Figure 40:
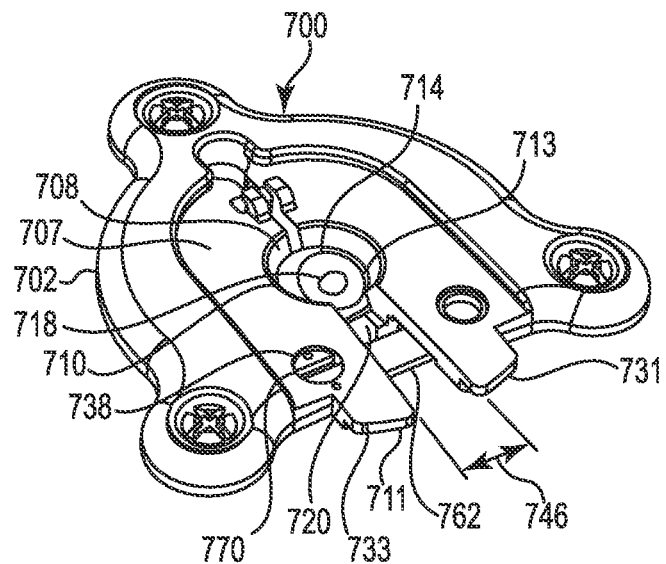
FIG. 40 is a partial (cap and medical device not shown) perspective view of the anchor of FIG. 38 in an expanded configuration.
Figure 41:
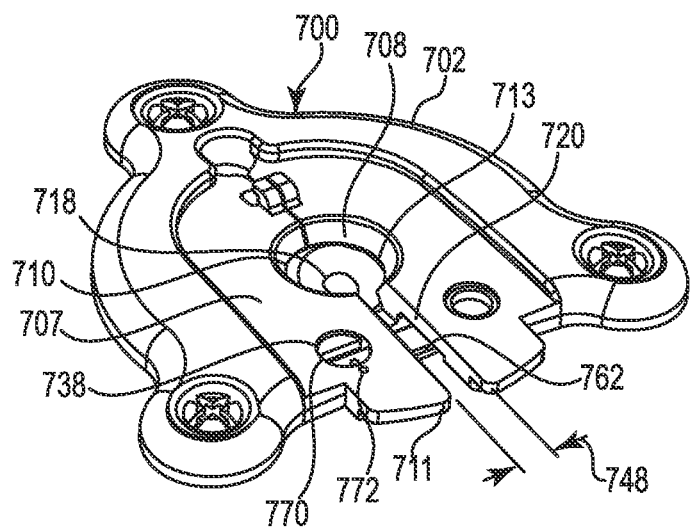
FIG. 41 is a partial perspective view of the anchor of FIG. 38 in a locked configuration.
Figure 42:
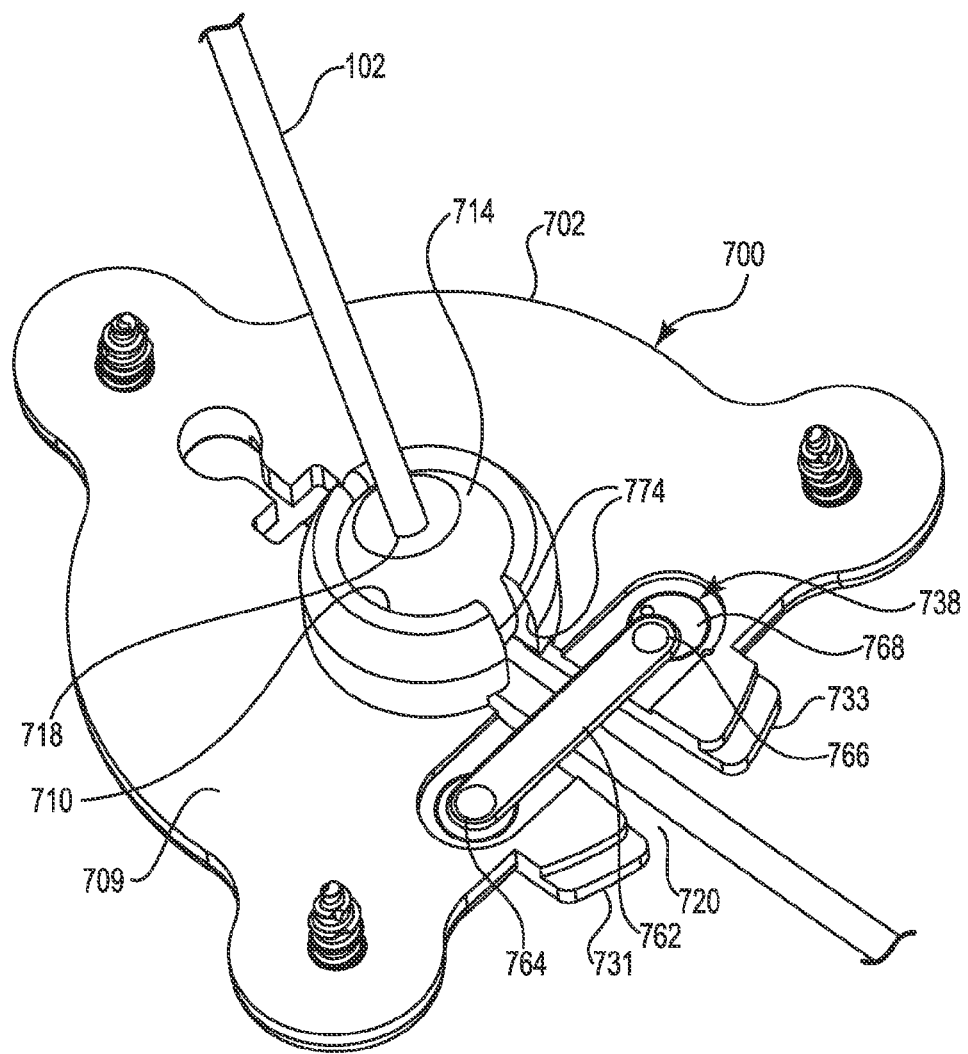
FIG. 42 is a bottom perspective view of the anchor of FIG. 40 (with medical device shown)

The base 702 may include an upper side 707, a lower side 709, a peripheral or outer edge 711 (see FIG. 39), and an inner edge 713 (see also FIG. 39). The inner edge 713 may define an opening 708 passing through the base 702 between the upper and lower sides 707 and 709, wherein the opening/inner edge further defines a socket 710 as is also shown in FIGS. 40-42. An optional cap or cover 705 may attach to the base 702 (e.g., to the upper side) after the medical device 102 is implanted. Even with the optional cap, the anchor 700 (and anchors 800 and 900 described below) may have a very patient-friendly, low profile, e.g., a height of about 2 mm.

The socket 710 may be configured to receive therein a retention member that forms or otherwise includes a convex or spherical surface 716 (see FIG. 39). In the embodiment illustrated in FIGS. 38-42, the retention member may once again form a ball-shaped or spherical member 714. The retention member (e.g., spherical member 714) is configured to be received within the socket 710 such that the retention member is operable, under certain circumstances, to rotate therein about three mutually perpendicular axes (see, e.g., axes x, y, and z of FIG. 4).

As with the spherical members 214, 314, 414, 514, and 614 described above, the retention member 714 may include a bore 718 formed therethrough. The bore 718 is configured to permit passage of the medical device (e.g., catheter or lead 102) through the base 702 from the upper side 707 to the lower side 709. Moreover, once again, the spherical member 714 may be positioned within the socket 710 such that an uppermost surface 715 of the retention member is at an elevation at or below the upper side 707 of the base as best seen in FIG. 39. Such a construction may better accommodate the cap 705.

As further shown in FIG. 39, the opening 708 may again be positioned to align coaxially with the burr hole 110. Moreover, the upper side 707 of the base 702 may define a passage extending from the inner edge 713 to and through the outer edge 711 as best illustrated in FIGS. 40-41. The passage may define a channel configured to receive therein the medical device (e.g., lead 102) as described in more detail below. The passage may be devoid of features, or could incorporate features useful to capturing a catheter connector such as connector 204, as described and illustrated herein.

In the illustrated embodiment, the passage is defined by a slot 720 extending radially from the socket through the outer edge and passing completely through the upper and lower sides 707, 709 as shown in FIGS. 40-41. Such a construction yields a split base 702 having a first side or portion 731 and a second side or portion 733 (also referred to herein as spaced-apart first and second portions), i.e., the base may form a U-shaped or C-shaped member when viewed from above. The split configuration is advantageous as it permits the effective diameter of the opening 708 to change merely by displacing the first portion 731 relative to the second portion 733 (e.g., selectively moving the first and second portions closer to (or farther away from) one another). For example, in the illustrated embodiment, the base 702 may form a slot 720 having a first width 746 corresponding to the anchor/base being in a first, e.g., expanded, configuration (see FIG. 40), and a second width 748 corresponding to the anchor/base being in a second, e.g., locked, configuration (see FIG. 41), wherein the second width is less than the first width. Once again, reducing the width of the slot 720 causes a corresponding reduction in the diameter of the socket 710. As a result, the spherical member 714 may be effectively clamped or squeezed by collapsing the split base 702 as described herein. As with the other anchors described herein, most any biocompatible material is suitable for the base 702, e.g., moldable thermoplastic (e.g., polysulfone or PEEK) or metal such as grade 2 or grade 5 Titanium. The spherical member 714 (as well as the members 814 and 914 described below), however, may be made from a soft, elastomeric material, e.g., silicone or urethane, for reasons further described below.

The spherical member 714 may function in a manner similar to the spherical members 214, 314, 414, 514, and 614 already described herein. In fact, as stated elsewhere, the various spherical members described and illustrated herein may be substituted for one another in other embodiments of the bases described herein without departing from the scope of the invention.

As shown in FIG. 39, the spherical member 714 may have a single bore 718 therein and it may function in a manner similar to the other retention members already described herein. However, instead of immobilizing the spherical member with a screw 238 or lock pin 538, the spherical member 714 may be immobilized via compression of the socket 710. Moreover, the spherical member 714 and bore 718 may be selected/sized to ensure that compression of the socket 710 also results in compression against the outer surface of the medical device 102 with sufficient force to immobilize the device relative to the spherical member.

To achieve reconfiguration of the base between the first, expanded (e.g., open) configuration (see FIG. 40) and the second, locked configuration (see FIG. 41), the anchor may include a lock mechanism 738 as perhaps best viewed in the bottom perspective view of FIG. 42. As shown in this view, the lock mechanism 738 may be configured to collapse the socket 710 to immobilize both: the spherical member 714 relative to the base 702; and the medical device 102 relative to the spherical member.

In the illustrated embodiment, the lock mechanism 738 is configured as an arm 762 connecting the first portion 731 to the second portion 733 of the base 702 by spanning across the slot 720. A first end 764 of the arm 762 is attached or connected (e.g., pivotally) to the first portion 731, while a second end 766 of the arm is attached or connected (e.g., pivotally) to the second portion 733 (e.g., to a cam or cam mechanism 768 attached to the second portion). The cam 768 may include tool features, e.g., a screw head 770 as shown in FIGS. 40-41, that permits the surgeon to manipulate the cam to collapse the socket 710 as further described below. That is to say, the cam mechanism may selectively displace, via the arm, the first portion 731 of the base relative to the second portion 733. The base 702 and/or cam 768 may also include indicia 772 (see FIG. 41), to visually indicate to the surgeon when the cam has been fully actuated, e.g., when the base has moved to its second, locked configuration shown in FIG. 41. In the illustrated embodiment, the indicia include marks on the screw head 770 and corresponding marks on the base than may align when the cam 768 is in a position corresponding to the base being in the first, expanded configuration and/or the second, locked configuration. The screw head 770 may rotate about 180 degrees between the first, expanded configuration and the second, locked configuration. To prevent the surgeon from overcompressing the socket 710, one or both of the first and second portions 731, 733 may include contacting stop members or surfaces 774 (see FIG. 42) that limit movement of the first portion the base 702 toward the second portion beyond the locked configuration.

The anchor 700 may ship with the base 702 in the first, expanded configuration shown in FIG. 40. In this configuration, the socket and spherical member are in an uncompressed state. That is, little or no compression is applied by the socket 710 on the spherical member 714. In one embodiment, the compression on the spherical member in the uncompressed state may be sufficient to ensure that the bore 718 frictionally engages the guide cannula 124 as further described below, but is not so excessive that it prevents sliding along the cannula or so excessive that the retention member 714 cannot rotate within the socket (e.g., about the three mutually perpendicular axes shown in FIG. 4). During implantation, however, when the cam is rotated 180 degrees from the position shown in FIG. 40 (corresponding to the base being in the first, expanded configuration) to the position shown in FIG. 41 (corresponding to the base being in the second, locked configuration), the socket 710 and spherical member 714 reconfigure to a compressed state. In the compressed state, the socket 710 applies sufficient compression to the spherical member 714 to compress the medical device 102 by reducing the bore 718 to effectively immobilize the device relative to the spherical member. Moreover, the socket 710 compresses sufficiently to effectively immobilize the spherical member 714 (within the socket 710) relative to the base.

FIGS. 43-49 diagrammatically illustrate an exemplary surgical lead implant procedure that may be used with the anchor 700 described above. Once again, the anchor 700 and lead 102 are illustrative only as the method is also applicable to the implantation of a catheter.

Figure 43:
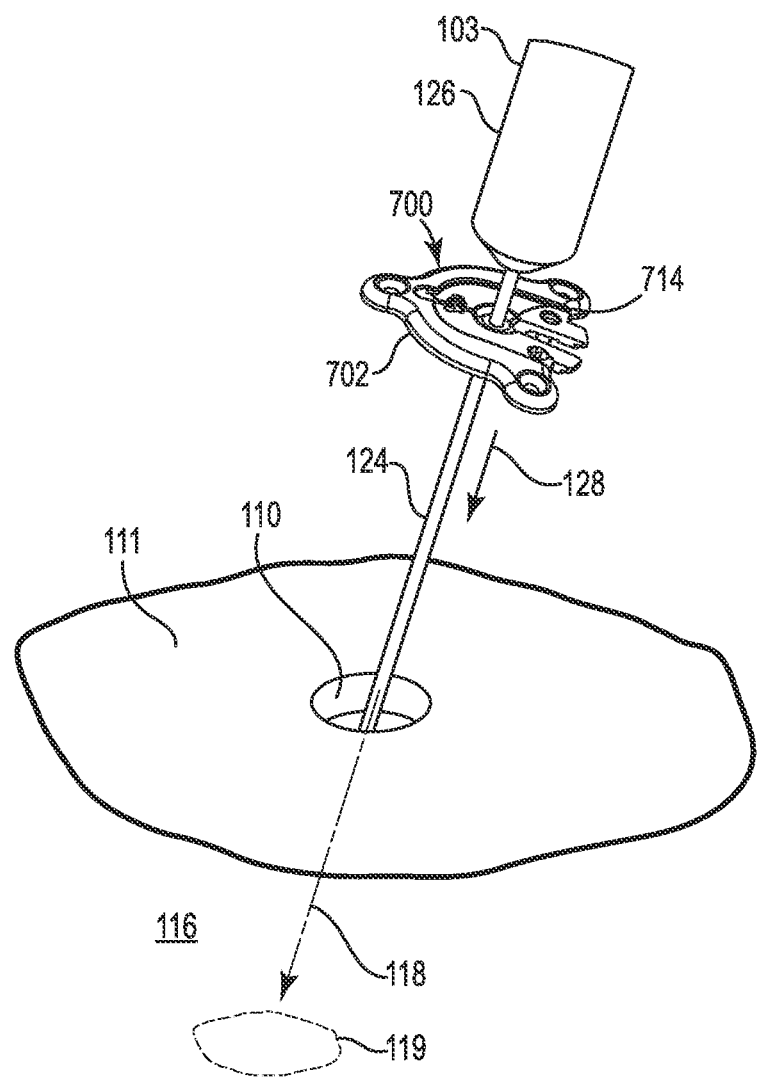

After forming the burr hole 110 in the skull 111, a guide cannula 124 may be attached to a headframe guide adapter 126 of the stereotactic apparatus 103 (see FIG. 1). The stereotactic apparatus 103 may be configured such that the guide cannula 124 aligns with the target tissue location 119 within the brain 116. That is, the guide cannula 124 may be configured such that its axis (i.e., the intended medical device trajectory 118) intersects with the target tissue location 119 as shown in FIG. 43. The anchor 700 (configured in the first, expanded configuration) may then be slid over a distal end of the guide cannula 124 (i.e., the distal end may be inserted through the bore 718 of the spherical member 714) and slid upwardly toward the guide adapter 126 before the distal end of the guide cannula is inserted into the burr hole 110. The guide cannula 124 may then be advanced until the distal end of the guide cannula is at or near a surface of the dura as shown in FIG. 43. The bore 718 of the spherical member 714 is, once again, sufficiently elastic to expand/deform to permit sliding entry of the guide cannula 124. The friction between the bore 718 and the guide cannula 124 is preferably sufficient to provide some resistance to unintended falling of the anchor toward the burr hole.

Figure 44:
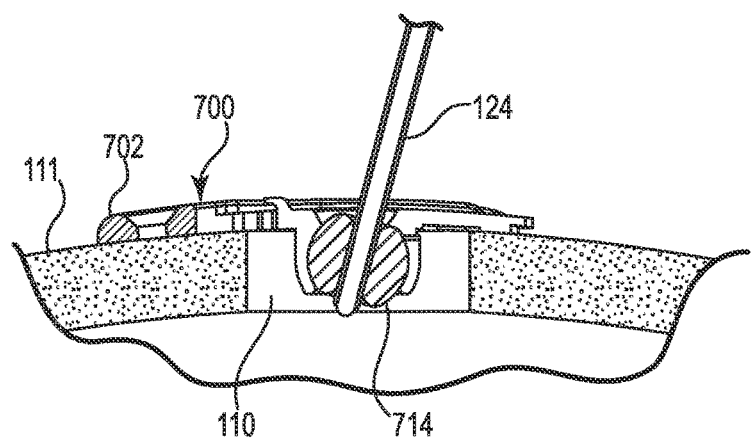

At this point, the surgeon may slide the anchor 700 down the guide cannula 124 toward the skull 11 surface as represented by arrow 128 in FIG. 43. The base 702 may then be rotated about the spherical member 714 until the base sits flush to the tissue (skull 111) surface as shown in FIG. 44.

Figure 45:
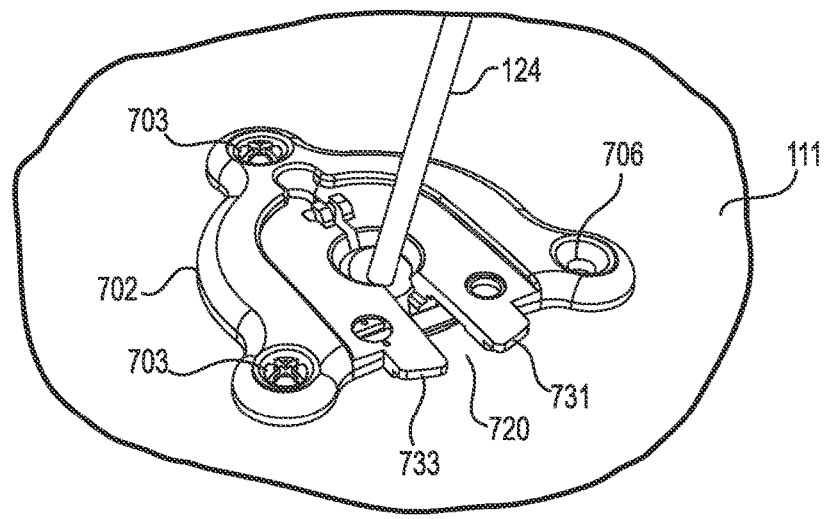

Once the base 702 is flush to the skull surface, the base may be secured to tissue, e.g., using two of the three bone screws 703 as shown in FIG. 45. One bone screw on one side (e.g., closest to the first side 731) of the slot 720 is not attached at this point to permit the base 702 to deflect to the second, locked configuration (see FIG. 41). The guide cannula 124 may then be advanced until its distal end is at or near the target tissue location 119. The lead 102 (or catheter) may then be inserted into the guide cannula 124 in accordance with known techniques until the therapy delivery tip 108 of the device 102 is at the target tissue location 119.

Figure 46:
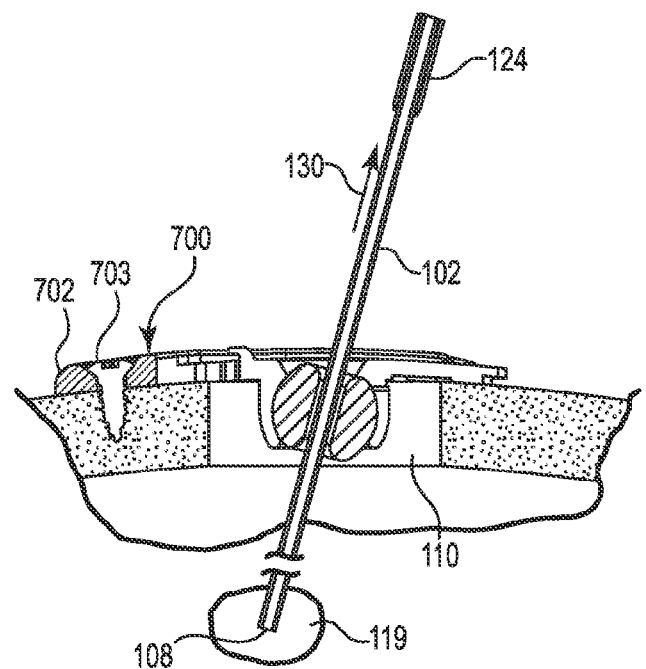

When the medical device 102 has been positioned, the guide cannula 124 may be retracted (moved in the direction 130) as shown in FIG. 46 while holding the catheter in place (e.g., with a stylet attached to the stereotactic apparatus 103 (see FIG. 1)). As the guide cannula 124 retracts beyond the bore 718, the elastomeric properties of the spherical member 714 cause the bore 718 to reduce in diameter. However, some clearance between the spherical member 714 and the device 102 may still exist, at least while the spherical member is in the uncompressed state. The stylet (not shown) may hold the medical device in place during cannula retraction.

Figure 47:
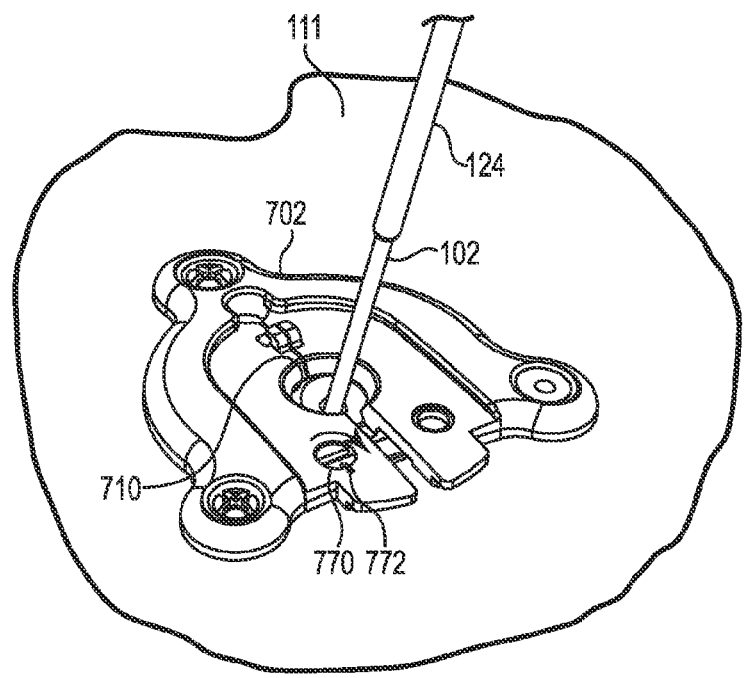

The surgeon may, at this point, rotate the screw head 770 of the cam 768 until the indicia 772 align as shown in FIG. 47. As the cam rotates, the base 702 moves from the first, expanded configuration of FIG. 40, to the second, locked configuration shown in FIG. 41. This movement results from the cam mechanism displacing the second end 766 of the arm from a first position corresponding to the expanded configuration of the base, to a second position corresponding to the locked configuration of the base. Once again, in this second, locked configuration, the socket 710 collapses sufficiently to compress the spherical member 714 against the medical device 102, immobilizing the medical device relative to the spherical member. Moreover, the spherical member 714 is compressed by the socket 710, immobilizing the spherical member relative to the socket/base. The medical device 102 is thus immobilized relative to the base 702.

Figure 48:
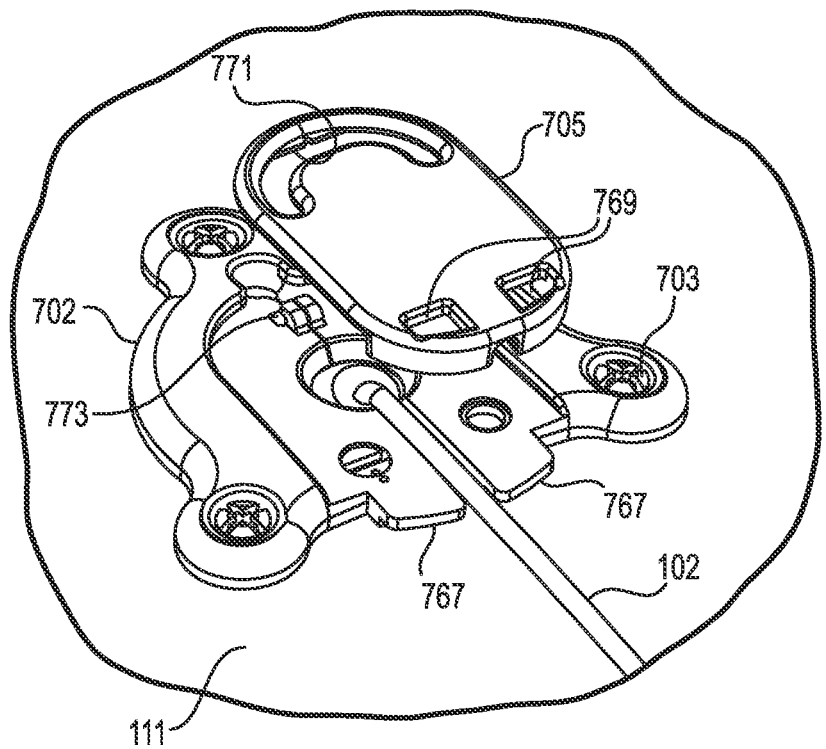
Figure 49:
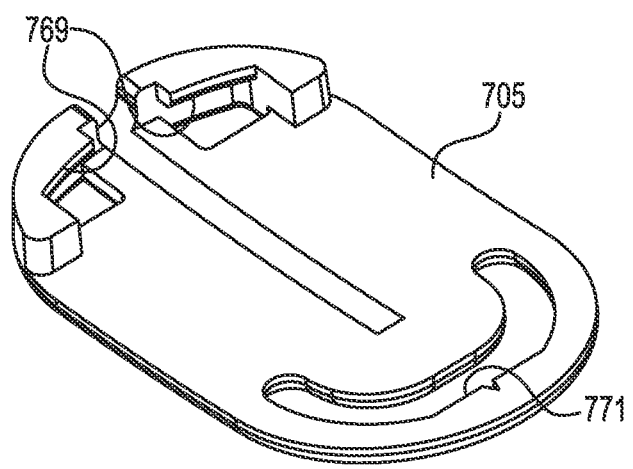

The stylet (not shown) may then be removed from the medical device 102 and the device bent and laid into the slot 720 as shown in FIG. 48 (i.e., the slot width is preferably selected to receive the medical device when the base is in the locked configuration). The optional cap 705 may then be attached to the base 702 and the medical device 102 attached to the therapy source 106 (see FIG. 1). The last screw 703 may then be inserted to secure the base in the second locked configuration as shown in FIG. 48.

In the illustrated embodiment, the cap 705 may be attached by engaging a tab 771 with a hook 773 on the base 702 (see FIG. 48) and then stretching the cap until slots 769 (see FIG. 49) formed in the cap engage tabs 767 of the first and second portions of the base. The cap 705 may be made of an acceptably stretchable material such as silicone. Alternatively, the cap could be rigid and rely on elongation of the portion of the cap containing the tabs 771 to accommodate attachment to the base.

FIGS. 50-55 illustrate an anchor system 801 including an anchor 800 in accordance with still yet another embodiment of the invention. Those of skill in the art will recognize similarities between the anchor 800 and the anchor 700 described above. In fact, in one embodiment, the anchor 800 differs from the anchor 700 only with respect to the lock member used to secure the anchor base in the second, locked configuration. One of skill in the art will appreciate that components of the anchor 800 may be substituted with components of the other embodiments described herein, and vice-versa, to produce yet additional embodiments without departing from the scope of the invention.

The anchor 800 is, like the anchor 700, described and illustrated in the context of an anchor for an electrical lead 102. However, as already stated, such an application is exemplary only and the anchor 800 could also be used to anchor a therapy catheter 102.

Figure 50:
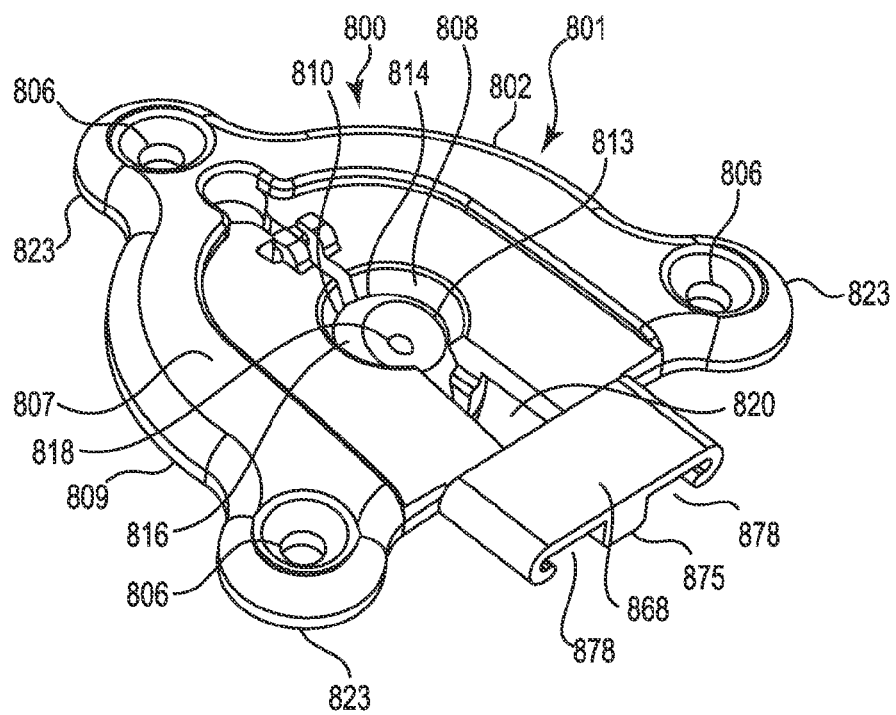
FIG. 50 is an upper perspective view of an anchor in accordance with still yet another embodiment of the invention, the anchor shown with a first clip installed.
Figure 51:
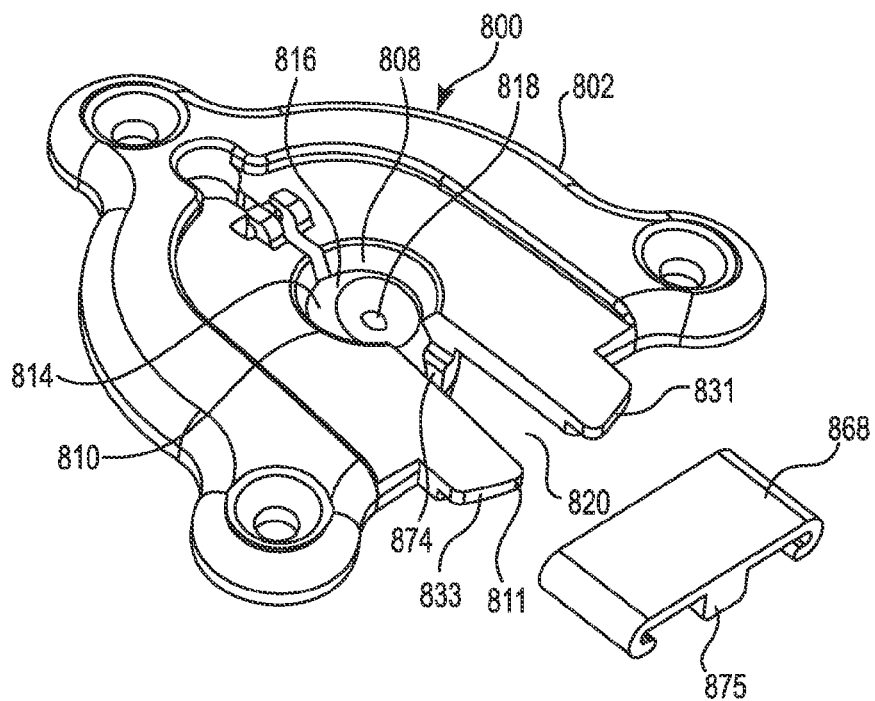
FIG. 51 is an upper perspective view of the anchor of FIG. 50 showing the first clip removed.

The anchor 800, once again, may include an annular base 802 that may be positioned to surround the burr hole 110 (not shown, but see FIG. 46 for analogous view). The anchor 800 (e.g., the base 802) is operable to secure to the tissue, e.g., to an outer surface of the skull 111, surrounding the burr hole 110 via any acceptable method. In the illustrated embodiment, the base 802 is secured with bone screws (not shown) extending through openings (e.g., holes 806) formed through the base 802 and threaded into the skull 111. In the illustrated embodiment, the holes 806 are formed in portions 823 of the base 802 that protrude outwardly as shown in FIG. 50.

The base 802 may include an upper side 807, a lower side 809, a peripheral or outer edge 811, and an inner edge 813. The inner edge 813 may define an opening 808 passing through the base 802 between the upper and lower sides 807 and 809, wherein the inner edge further defines a socket 810. The optional cap or cover 705 may attach to the base 802 to cover the opening 808 as already described above.

The socket 810 may be configured to receive therein a retention member that forms or otherwise includes a convex or spherical surface 816. In the embodiment illustrated in FIGS. 50-55, the retention member may once again form a ball-shaped or spherical member 814. The retention member (e.g., spherical member 814) is configured to be received within the socket 810 such that the retention member is operable, under certain circumstances, to rotate therein about three mutually perpendicular axes (see, e.g., axes x, y, and z of FIG. 4).

The spherical member 814 is similar in most respects to the spherical member 714 already described herein (e.g., the member 814 includes a bore 818 sized to receive the medical device 102/guide cannula 124 in substantially the same way). As a result, no further description is provided herein. Moreover, the base 802 includes a passage or channel, e.g., slot 820, extending from the inner edge 813 to and through the outer edge 811 that results in a split base (forming a U-shaped or C-shaped member when viewed from above) as already described above with reference to anchor 700. As a result, no further description is provided with respect to aspects of the anchor 800/base 802 that are common with the anchor 700/base 702. In fact, for the most part, those items identified with a reference numeral 8xx will be similar to the same item identified with the number 7xx (e.g., bore 818 is similar to bore 718, retention member 814 is similar to retention member 714, etc.), unless otherwise identified herein.

As stated previously, the anchor 800 does differ from the anchor 700 primarily with respect to the lock mechanism. In the anchor 700, the lock mechanism 738 includes the cam 768, while in the anchor 800, the lock mechanism is configured as a clip or clips connecting a first portion 831 of the base 802 to a second portion 833 of the base by spanning across the slot 820 as shown in FIG. 50. A first or "open" clip 868 (see FIGS. 50-53) may include one or more openings 878 that engage protrusions or protruding ears of the first portion 831 and second portion 832 of the base 802 to hold the base in the first, expanded configuration, e.g., by holding the first portion in fixed relation relative to the second portion. The first clip 868 may also include a spacer 875 that slides into the slot 820 and prevents the first and second portions 731, 733 from moving towards one another.

The system 801 may also include a second or lock clip 876 (see FIG. 54) that includes a narrower opening 880 that engages the protruding ears of the first and second portions 831, 833 to correspondingly hold the base in a second, locked configuration (an additional clip could be provided to hold the base in another configuration between the expanded and locked configurations if desired). The first and second portions 831, 833 may again include contacting surfaces 874 (only visible on one side in FIG. 51) that may limit the amount of compression the base 802 may apply to the socket 810.

The anchor 800 may ship with first clip 868 attached to the base 802 such that the base is in the first, expanded configuration as shown in FIG. 50. In this configuration, the socket 810/spherical member 814 are in the uncompressed state, e.g., compression on the socket 810 is sufficient to ensure the bore 818 can frictionally engages the guide cannula 124 (see FIG. 53) as further described below, but is not so excessive that the retention member 814 cannot rotate within the socket. During implantation, however, the second clip 876 may replace the first clip 868. When this occurs, the base 802 is moved to the second, locked position wherein the socket 810 applies sufficient compression to the retention member 814 to compress the medical device 102 within the bore 818 and effectively immobilize the device 102 relative to the spherical member (i.e., the socket 810/spherical member 814 moves to the compressed state). Moreover, the socket 810 compresses sufficiently to effectively immobilize the spherical member 814 within the socket 810.

During implantation, the anchor 800 operates using a procedure similar to that described with respect to the anchor 700. Accordingly, the procedure described with reference to FIGS. 43-49 applies also to the anchor 800, with the following distinctions.

Figure 52:
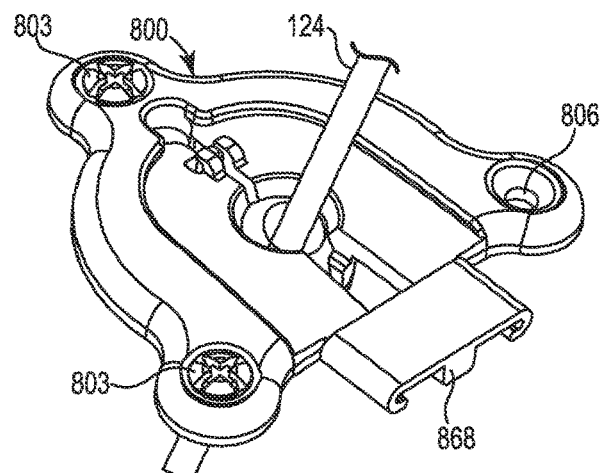
FIG. 52 is an upper perspective view of the anchor of FIG. 50 after implanting of a medical device and initial attachment of the anchor to tissue.
Figure 53:
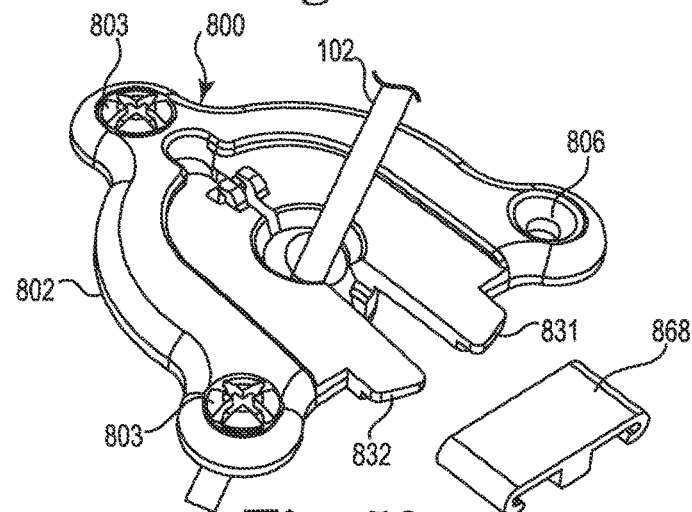
FIG. 53 is an upper perspective view of the anchor of FIG. 52 after further removing the first clip.
Figure 54:
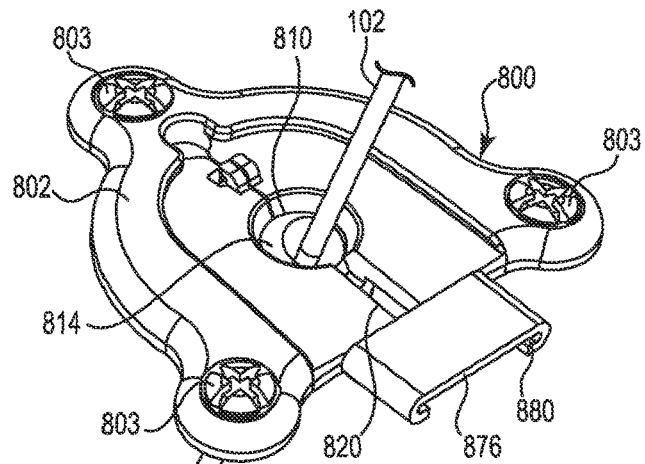
FIG. 54 is an upper perspective view of the anchor of FIG. 53 after attachment of a second clip and final attachment of the anchor to the tissue.

The anchor 800 may have attached thereto the first clip 868 as shown in FIG. 50 when it is slid over the cannula as shown in FIGS. 43 and 52. After the base 802 is moved to the skull 111 and has been secured with two of the three screws 806, the lead has been implanted, and the guide cannula retracted, the surgeon may remove the first clip 868 as shown in FIG. 53. The first and second portions 831, 833 may then be pinched together and the second or lock clip 876 slid over the base 802 as shown in FIG. 54. With the second clip 876 so attached, the base 802 moves from the first, expanded configuration of FIG. 52, to the second, locked configuration shown in FIG. 54. In this second configuration, the socket 810 collapses sufficiently to compress the retention member 814 against the medical device 102, immobilizing the latter relative to the former. Moreover, the retention member 814 is compressed by the socket, immobilizing the former relative to the latter. The medical device is thus immobilized relative to the anchor 802.

The third screw 803 may then be threaded into the tissue as shown in FIG. 54, securing the base in the second configuration. Once the third screw is tightened, the second clip 876 may be removed.

Figure 55:
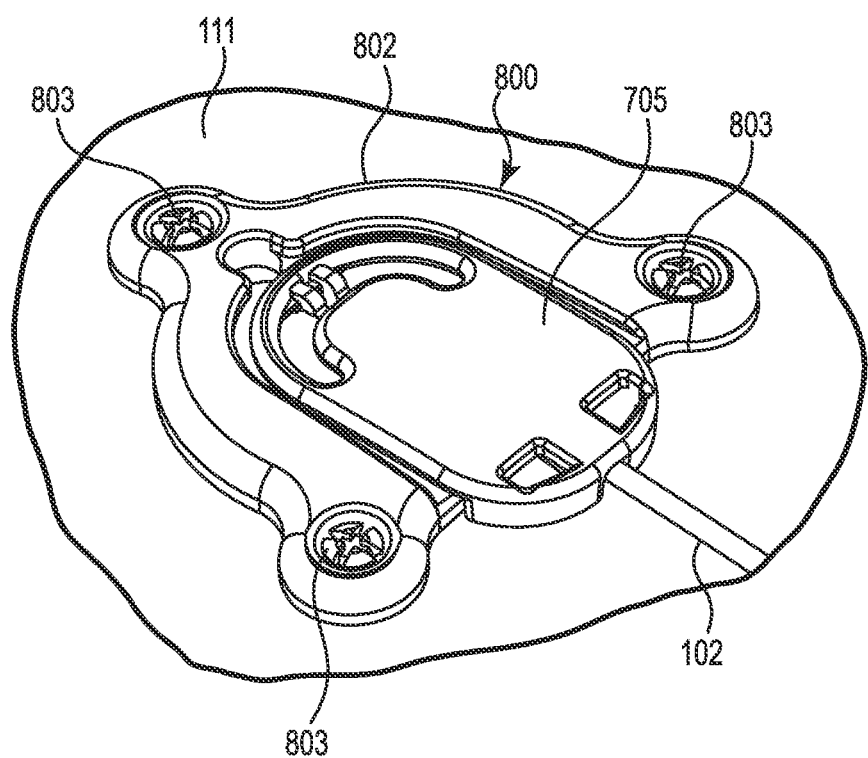
FIG. 55 is an upper perspective view of the anchor of FIG. 54 after removal of the second clip, routing of the medical device, and attachment of an optional cap.

The stylet (not shown) may then be removed from the medical device 102 and the device bent and laid into the slot 820. The optional cap 705 may then be attached to the base 802 as shown in FIG. 55, and the medical device 102 attached to the therapy source 106 (see FIG. 1). In the illustrated embodiment, the cap 705 may be attached to the base in the same manner described herein with respect to the base 702.

Figure 56:
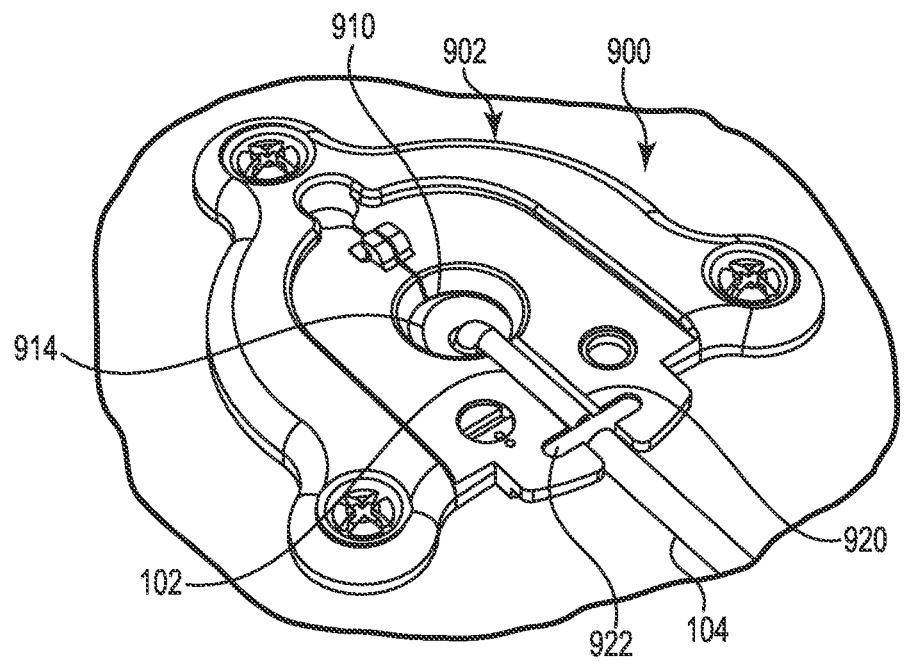
FIG. 56 is an upper perspective view of a catheter anchor in accordance with yet still another embodiment of the invention.
Figure 57:
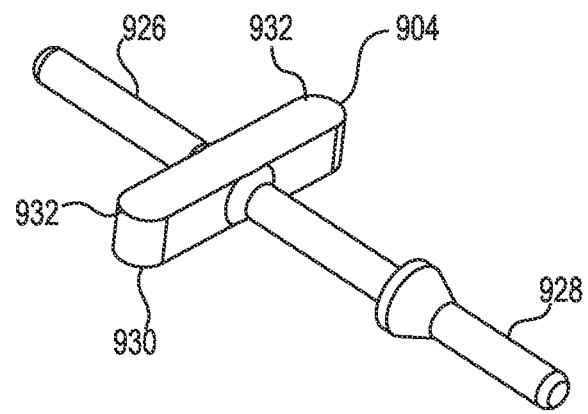
FIG. 57 is a perspective view of a catheter connector for use with the anchor of FIG. 56.

FIGS. 56-57 illustrate an anchor 900 that is a variation of the anchor 700 revised to accommodate anchoring of a therapy catheter 102 and connection of the same with a delivery catheter 104. Once again, only those aspects that differ from the anchor 700 will be described.

As shown in FIG. 56, the anchor 900 may again include a base 902 having a slot 920 similar to the slot 720, and a spherical member 914 contained within a socket 910 of the base. However, the slot 920 may include a relief 922 configured to accommodate ears or protruding portions 932 of a central portion 930 of a connector 904 that is shown in more detail in FIG. 57. The connector 904 may include a first end 926 for fluidly coupling to the therapy catheter 102, and second end 928 for fluidly coupling to the delivery catheter 104.

During implantation, the anchor 900 may be moved to the second, locked configuration (as shown in FIG. 56) after the therapy catheter is positioned and the guide cannula is removed as described above with reference to the anchor 700. After stylet removal from the therapy catheter 102, the catheter may be laid into the slot 920 and cut to length at the relief 922. The first end 926 of the connector 904 may then be manually inserted into a lumen of the cut end of the therapy catheter 102. The connector 904 may then be placed into the slot 920, where it may be received with a clearance fit. The second end 928 of the connector may then be connected to the delivery catheter by placing the lumen of the delivery catheter over the second end. Once the catheters 102, 104 are connected, an optional cap (see, e.g., cap 705) may be attached to the base 902 as already described herein, and the delivery catheter attached to the therapy source 106 (see FIG. 1). The cap 705 may capture and retain the connector 904 in place. Moreover, the central portion 930 of the connector 904 may reduce or prevent the transmission of axial loads from the delivery catheter 104 to the therapy catheter 102.

Burr hole anchors and systems in accordance with embodiments of the present invention may provide various benefits including, for example, reducing or eliminating biasing forces applied to an implanted medical device that tend to result in device migration or lateral compression of brain tissue near the entry point. As a result, the delivering tip of the therapy catheter may be less likely to be displaced during the implantation period. Such a benefit is realized regardless of device trajectory through the burr hole, offering greater surgical flexibility in burr hole placement relative to target tissue location. Moreover, retention members like those described herein may also assist with holding the medical device during the remainder of the anchoring process without the use of specialized surgical tools. Still further, embodiments such as those described herein are well-suited to immobilizing both leads and catheters as they achieve immobilization by compressing the medical device along a relatively soft, elastomeric cylindrically-shaped contact area as opposed to holding mechanisms that use a more rigid, two point contact configuration.

Yet still further, anchors and systems in accordance with embodiments of the present invention may be cost-effective to produce. For example, the bases and retention members described herein may be produced through injection molding manufacturing, permitting low cost production of multiple sizes (e.g., primate and human). Moreover, there is no requirement for internal anchor tubing to connect the delivery catheter to the therapy catheter. As a result, potential leak points may be avoided.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are described and reference has been made to possible variations within the scope of this invention. These and other variations, combinations, and modifications of the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A sub-dermal anchor configured to secure a medical device implanted via a portal formed in a mammalian body, the anchor comprising:
   a base configured to secure to tissue surrounding the portal, the base comprising an upper side, lower side, outer edge, and inner edge, the inner edge defining an opening passing between the upper and lower sides, the opening forming a socket, wherein the base is a single, unitary base; and
   an elastomeric retention member comprising a spherical surface, the retention member configured to be received within the socket such that the retention member may rotate therein about three mutually perpendicular axes, the retention member defining a bore formed therethrough, the bore configured to permit passage of the medical device through the base from the upper side to the lower side; wherein the retention member is positioned within the socket such that an uppermost surface of the retention member is at an elevation below the upper side of the base and the retention member is recessed into the portal;
   wherein the sub-dermal anchor is adapted to be implanted sub-dermally on the mammalian body.

2. The anchor of claim 1, wherein the upper side of the base defines a passage extending from the inner edge to the outer edge, the passage configured to receive therein the medical device.

3. The anchor of claim 2, further comprising a connector configured for captivation within the passage.

4. The anchor of claim 1, further comprising a lock member configured to lock the retention member relative to the base.

5. The anchor of claim 1, wherein the bore of the retention member is configured to receive the medical device with an interference fit.

6. The anchor of claim 1, wherein the retention member comprises a ball-shaped member.

7. The anchor of claim 1, wherein the retention member comprises a separate sleeve defining at least part of the bore, the sleeve configured to frictionally engage the medical device.

8. The anchor of claim 7, wherein the retention member comprises a first material and the sleeve comprises a second material different than the first material.

9. The anchor of claim 7, wherein inner surfaces of the retention member form retaining portions configured to receive and retain the sleeve.

10. The anchor of claim 1, wherein the retention member comprises two mating semi-spherical halves that join to form a uniform, ball-shaped retention member.

11. The anchor of claim 10, further comprising a cylindrical sleeve contained between the two semi-spherical halves, wherein an inner surface of the sleeve forms the bore and is configured to frictionally receive the medical device.

12. The anchor of claim 1, wherein the retention member is truncated such that its uppermost surface comprises a planar surface, the planar surface including two or more bores.

13. The anchor of claim 1, wherein the portal is formed in a skull of the mammalian body, wherein the anchor is adapted to extend above an outer surface of the skull a distance of about 2-3 mm.

* * * * *